US012128158B2

(12) United States Patent
Davison et al.

(10) Patent No.: US 12,128,158 B2
(45) Date of Patent: *Oct. 29, 2024

(54) METHOD OF MAKING AN OSTEOCONDUCTIVE FIBROUS ARTICLE AND A MEDICAL IMPLANT COMPRISING SUCH OSTEOCONDUCTIVE FIBROUS ARTICLE

(71) Applicant: DSM IP Assets B.V., Heerlen (NL)

(72) Inventors: Noel L. Davison, Echt (NL); Henricus Johannes Arts, Echt (NL); Aylvin Jorge Angelo Athanasius Dias, Echt (NL); Anne Marie Persson, Echt (NL); Ruud Jozef Regina Wilhelmus Peters, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/108,038

(22) Filed: Feb. 10, 2023

(65) Prior Publication Data
US 2023/0270920 A1    Aug. 31, 2023

Related U.S. Application Data

(63) Continuation of application No. 16/753,355, filed as application No. PCT/EP2018/077216 on Oct. 5, 2018.

(30) Foreign Application Priority Data

Oct. 6, 2017 (EP) .................... 17195330

(51) Int. Cl.
A61L 31/08 (2006.01)
A61L 17/04 (2006.01)
A61L 17/14 (2006.01)
A61L 27/18 (2006.01)
A61L 27/32 (2006.01)
A61L 27/34 (2006.01)
A61L 31/06 (2006.01)
A61L 31/10 (2006.01)
C08L 75/04 (2006.01)

(52) U.S. Cl.
CPC ............ *A61L 31/086* (2013.01); *A61L 17/04* (2013.01); *A61L 17/145* (2013.01); *A61L 27/18* (2013.01); *A61L 27/32* (2013.01); *A61L 27/34* (2013.01); *A61L 31/06* (2013.01); *A61L 31/10* (2013.01); *C08L 75/04* (2013.01); *A61L 2420/02* (2013.01); *A61L 2430/02* (2013.01); *A61L 2430/38* (2013.01)

(58) Field of Classification Search
None
See application file for complete search history.

(56) References Cited

U.S. PATENT DOCUMENTS

| 3,839,068 A | 10/1974 | Miura |
| 4,024,871 A | 5/1977 | Stephenson |
| 4,739,013 A | 4/1988 | Pinchuk |
| 4,810,749 A | 3/1989 | Pinchuk |
| 5,133,742 A | 7/1992 | Pinchuk |
| 5,229,431 A | 7/1993 | Pinchuk |
| 5,298,028 A | 3/1994 | Hsu |
| 5,779,729 A | 7/1998 | Severini |
| 6,296,667 B1 | 10/2001 | Johnson et al. |
| 7,048,792 B2 | 5/2006 | Axen et al. |
| 8,562,647 B2 | 10/2013 | Kaiser et al. |
| 2001/0001113 A1 | 5/2001 | Lim et al. |
| 2003/0220700 A1 | 11/2003 | Hammer et al. |
| 2004/0228905 A1 | 11/2004 | Greenspan et al. |
| 2006/0034931 A1 | 2/2006 | Hansen |
| 2006/0210816 A1* | 9/2006 | Finley ............... A61L 27/34 428/521 |
| 2006/0216321 A1 | 9/2006 | Lyu et al. |
| 2011/0022085 A1 | 1/2011 | Murphy et al. |
| 2011/0251639 A1* | 10/2011 | Thomas ............ A61L 17/12 606/228 |
| 2016/0144066 A1 | 5/2016 | Long et al. |
| 2016/0271296 A1 | 9/2016 | Jongpaiboonkit et al. |
| 2016/0287242 A1 | 10/2016 | Troxel et al. |

FOREIGN PATENT DOCUMENTS

| DE | 10055465 A1 | 5/2002 |
| JP | H06339521 | 12/1994 |
| JP | H06339521 A | 12/1994 |
| JP | H06339522 | 12/1994 |
| JP | H06339522 A | 12/1994 |
| JP | 2014193272 A | 10/2014 |
| WO | 0048552 A1 | 8/2000 |
| WO | 02070031 A1 | 9/2002 |
| WO | 03103738 A1 | 12/2003 |
| WO | 2006020644 A2 | 2/2006 |
| WO | 2014060591 A1 | 4/2014 |

OTHER PUBLICATIONS

Bharati et al. Journal of the European Ceramic Society 2009 29:2527-2535 (Year: 2009).*
American elements reference, www.americanelements.com/boiling-point.html, 2014, pp. 1-3.

(Continued)

*Primary Examiner* — Melissa S Mercier
*Assistant Examiner* — Caralynne E Helm
(74) *Attorney, Agent, or Firm* — Kevin M. Bull

(57) ABSTRACT

The disclosure relates to a method of making a bioceramic coating on a fibrous article for use in a medical implant, comprising steps of providing an article comprising fibers made from a biocompatible, non-biodegradable polymer; coating at least the fibers that will be in contact with bone upon use as an implant with a solution of a coating polymer to result in coated fibers having a coating polymer layer; treating the coated fibers with a dispersion of bioactive ceramic particles 0.01-10 μm in a treating solvent comprising a solvent for the coating polymer in at least one step; and substantially removing the treating solvent; to result in the particles being partly embedded in the coating polymer layer of the coated fibers.

22 Claims, 5 Drawing Sheets

(56) References Cited

OTHER PUBLICATIONS

Solvents Reference, People.chem.umass.edu/xray/solvent.html, 2012, p. 1.
Acetic Acid: www.ilo.org/dyn/iscs/showcard.display?p_lang=en&p_card_id=0363&p_version=2, (Year:2010).
Aydin et al, Interaction of Osteoblasts with Macroporous Scaffolds Made of PLLA/PCL Blends Modified with Collagen and Hydroxyapatite;, Advanced Engineering Materials, 2009, pp. B83-B88, 11 (8).
Barnes et al, Using scratch testing to measure the adhesion strength of calcium phosphate coatings applied to poly(carbonate urethane) substrates, Journal of Mechanical Behavior of Biomedical Materials, 2012, pp. 128-138, 6.
Blaker, J.J., et al., Development and characterization of silver-doped bioactive glass-coated sutures for tissue engineering and wound healing applications, Biomaterials, 2004, p. 1319-1329, 25.
Boccaccini, et al, Composite Surgical Sutures with Bioactive Glass Coating, Journal of Biomedical Materials Research Part B: Applied Biomaterials, 2003, pp. 618-626, 67B.
Bretcanu, et al, Bioactivity of degradable polymer sutures coated with bioactive glass, Journal of Materials Science: Materials in Medicine, 2004, pp. 893-899, vol. 15.
Chen, et al, Bioactive and Mechanically Strong Bioglass—Poly (D,L-Lactic Acid) Composite Coatings on Surgical Sutures, Journal of Biomedical Materials Research Part B: Applied Biomaterials, 2006, pp. 354-363, 76B.
Chetty et al, 2007, Hydroxyapatite-coated polyurethane for auricular cartilage replacement: An in vitro study, Journal Biomedical Materials Research Part A, 2007, pp. 475-482, (DOI 10.1002/jbm.a).
Davison, et al, In vivo performance of microstructured calcium phosphate formulated in novel water-free carriers, Acta Biomaterialia 8, 2008, pp. 2759-2769, (DOI: 10.1016/j.actbio.2012.04.007).
Debbabi et al, Simultaneous optimization of mechanical properties of braided polyethylene terephthalate suture subjected to hot-stretching treatment, Journal of Industrial Textiles, 2016, pp. 1417-1439, 45(6).
Dorozhkin, S.V., Calcium orthophosphate deposits: Preparation, properties and biomedical applications, Materials Science and Engineering C, 2015, 272-326, C55.
Geary et al. Mater. Sci: Mater. Med (2008) 19:3355-3363 (DOI 10.1007/s10856-008-3472-8).
Jonathan Pratten, In Vitro Attachment of Staphylococcus epidermidis to Surgical Sutures with an without Ag- containing Bioactive Glass Coating, Journal of Biomaterials Applications, Jul. 2004, pp. 47-57, vol. 19.
Li et al, Biomedical coatings on polyethylene terephthalate artificial ligaments, Journal of Biomedical Materials Research A, Feb. 2015, pp. 839-845, vol. 103 A, Issue 2 (DOI: 10.1002/jbm.a.35218).
Li et al, Enhancement of the osseointegration of a polyethylene terephthalate artificial ligament graft in a bone tunnel using 58S bioglass, International Orthopaedics (SICOT), 2012, pp. 191-197, (DOI: 10.1007/s00264-011-1275-x).
Li et al., Hydroxyapatite coating enhances polyethylene terephthalate artificial ligament graft osseointegration in the bone tunnel, International Orthopaedics, 2010, pp. 1561-1567, (DOI: 10.1007/s00264-010-1158-6).
Pfeiffer, et al., The histologic and biomechanical response of two commercially available small glenoid anchors for use in labral repairs, Journal of Shoulder and Elboe Surgery, . 2014, pp. 1156-1161, DOI: 10.1016/j.jse.2013.12.036).
Q.Z. Chen, J.J. Blaker, A. R. Boccaccini, Bioactive and Mechanically Strong Bioglass-Poly(D,L-Lactic Acid) Composite Coatings on Surgical Sutures, Department of Materials and Center for Tissue Engineering and Regenerative Medicine, imperial College London, Sep. 13, 2005, pp. 354-363.
Wu Yang et al., The Effect of Bioactive Glass Modified Polyethylene Terephthalate on Bone Healing, Chinese Excellent Doctoral Dissertation Full-text Database (Master) Medical Science and Technology Series, Mar. 15, 2013, pp. 11-16, vol. 3.
Yilgor, et al., Structure-Morphology-Property Behavior of Segmented Thermoplastic Polyurethanes and Polyureas Prepared without Chain Extenders, Polymer Reviews, 2007, pp. 487-510, vol. 47.
Brito, et al., Chlorhexidine-loaded bioactive glass for incorporation into adhesive systems: Mechanical properties, antibacterial activity, cell viability, and hydroxyapatite precipitation,, Int'l Journal of Adhesion & Adhesives,, 124, 103354, 2023.
E. Ingham et al., The role of macrophages in osteolysis of total joint replacement, Biomaterials,, 26(11), pp. 1271-1286., 2005.
J.H. Werner, et al., Agrawal, Immunobiology of periprosthetic inflammation and pain following ultra-high-molecular-weight-polyethylene wear debris in the lumbar spine,, Expert Rev Clin Immunol, 14(8), pp. 695-706, 2018.
Krupa-Zuczek, et al., Manufacturing of phosphoric acid from hydroxyapatite, contained in the ashes of the incinerated meat-bone wastes, Polish Journal of Chemical Technology, vol. 10, 3, pp. 13-20, 2008.
Moritz et al., Mesoporous silica materials with different structures as the carriers for antimicrobial agent. Modeling of chlorhexidine adsorption and release, Applied Surface Science, 356, pp. 1327-1340, 2015.
N. Marsidi et al., Measuring forces in suture techniques for wound closure., Journal of Surgical Research, (255), pp. 135-154. https://doi.org/10.1016/j.jss.2020.05.033, Nov. 2020.
Ntalos, et al., Conventional rotator cuff versus all-suture anchors—A biomechanical study focusing on the insertion angle in an unlimited cyclic model, PLoS One, e0225648, https://doi.org/10.1371/journal.pone.0225648, 2019.

* cited by examiner

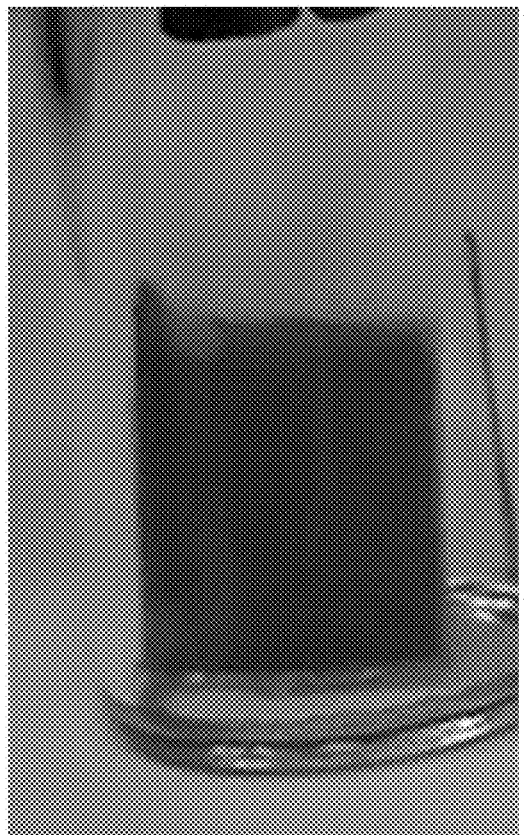
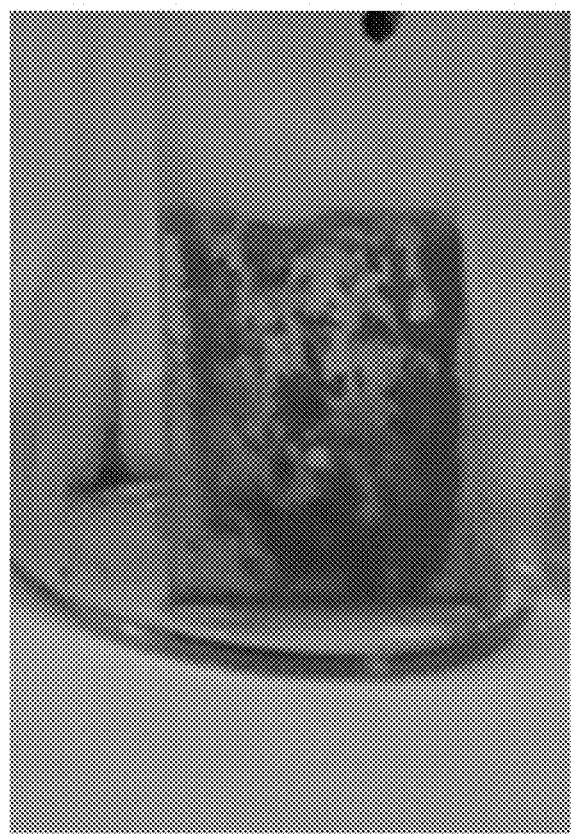
Fig. 1A
Fig. 1B

METHOD OF MAKING AN OSTEOCONDUCTIVE FIBROUS ARTICLE AND A MEDICAL IMPLANT COMPRISING SUCH OSTEOCONDUCTIVE FIBROUS ARTICLE

CROSS-REFERENCE TO RELATED APPLICATIONS

This application is a continuation of U.S. application Ser. No. 16/753,355, filed 3 Apr. 2020, now U.S. Pat. No. 12,016,977, which is a U.S. national phase entry under 35 USC 371 of international application PCT/EP2018/077216, filed 5 Oct. 2018, which designated the U.S. and claims priority to European Application 17195330.0, filed 6 Oct. 2017, the entire contents of each of which is hereby incorporated by reference in its entirety.

FIELD

The disclosed inventions relate to methods of making a fibrous article showing bioactivity like osteoconductive properties for use in a medical implant, especially to a polyester fibrous article having a coating with bioactive inorganic particles like calcium phosphates to enhance bone growth on the article after implantation. The inventions also relate to such bioactive fibrous articles made, to their uses in making medical implants, and to such medical implants as made like flexible tissue anchors, bone fixation devices, and textile-based scaffolds for bone regeneration.

BACKGROUND

Fibrous articles, like braided cables or knitted and woven textile constructs made from fibers or filaments spun from synthetic polymers, have found various applications as a component of a medical device, such as in surgical sutures and cables, artificial ligaments and tendons, hernia meshes, and flexible tissue anchors.

A tissue anchor as used in orthopedic surgery is an implantable medical device that for example is applied to re-attach soft tissue like a tendon to bone or to attach an artificial tendon to bone, as in shoulder instability repair or knee ligament reconstruction. Attachment to bone is typically obtained by inserting the anchor into a hole drilled in the bone (also called bore or tunnel) and connecting to soft tissue via a suture attached to the anchor. A tissue anchor may be rigid and non-flexible, like a solid screw or plug molded from metal or biocompatible polymer. A disadvantage of these rigid anchors is that relatively large holes need to be made in the bone. Alternatively, flexible anchors, such as a fibrous article comprising fibers spun from a biocompatible polymer are applied, which generally require significantly smaller bone tunnels, while providing at least similar strength.

In U.S. Pat. No. 8,562,647B2 a flexible anchor is described, which comprises a fibrous body or sleeve defining a passage through which a suture construct passes and to which it is connected, at least one self-locking adjustable loop, and leg portions. After inserting into a bore in a bone, an anchoring mass is formed by changing the shape of the flexible anchor by applying tension to the adjustable loop via pulling on the ends of the connected suture. The suture construct and fibrous sleeve are typically made by braiding multiple strands of non-resorbable, biocompatible polymer fibers; like a polyester, more specifically a polyethylene terephthalate (PET) polymer or copolymer. Such fiber-based flexible tissue anchor is often referred to as an 'all-suture anchor' (ASA) in the art.

Implants or components thereof made from PET or other synthetic polymers are generally bioinert and do not intrinsically bind to bone. Consequently, unmodified PET-based orthopedic implants, like an ASA, are prone to fibrous tissue encapsulation after implantation because of foreign body response in the bore. Without strong bonding between host bone and implant, continuously changing loads and/or micromotion of the implant may lead to implant instability and loosening, bore widening, and cyst formation (see e.g. Pfeiffer et al, DOI: 10.1016/j.jse.2013.12.036).

From biological perspective, the ideal material for reconstructive surgery is autogenic bone or tissue, because of biocompatibility, osteoconductivity, osteoinductivity and lack of immunogenic response. Limitations in harvesting adequate amounts of tissue or bone material and disadvantages of multiple operations, however, make the 'ideal' material far from ideal for many surgical procedures. An alternative is using allogeneic and xenogeneic bone-derived grafts, but such materials may induce disease transfer, high immunogenic response, or show unreliable degradation behavior. Therefore, synthetic implant materials or biomaterials, like metals, ceramics, polymers and composites, find increasing use in clinical applications. Several bioactive materials have been clinically applied as e.g. bone fillers and bone graft substitutes for quite some years, because they do not illicit foreign body encapsulation by the host but rather bond directly to bone due to their reactive, biomimetic surfaces. Such osteoconductive materials allow native bone tissue to bond and grow on the material surface resulting in osseointegration; i.e. mechanical anchorage of the implant in bone. Examples of such biomaterials include calcium phosphates like hydroxyapatite, mixed inorganic oxides like Bioglass®, and composites of polymer and such bioactive inorganic materials.

Most synthetic polymers as such are not bioactive but bioinert, and therefore do not bond to bone but are rather encapsulated by fibrous tissue. To overcome this shortcoming in orthopedic use, composites of polymer and bioactive materials have been shown to potentially combine the desired biological effects of the bioactive materials along with inherent advantages of polymers, including the option to tailor properties by varying composition and addition of further compounds, and freedom in design, processing and shaping.

Polymer-ceramic composites as bioactive material may be made by mechanical mixing of polymer and ceramic particles, generally resulting in a polymer continuous matrix with bioactive ceramic (also called bioceramic) particles dispersed therein. Mixing may be done by processing in the melt state of the polymer, but also in solution or dispersion to allow lower processing temperature. Spinning of fibers, however, is often hampered by the particulate loading, for example leading to instabilities and frequent breakage in the spinning process. Other disadvantages of such composites may include undesired changes in bulk properties. Incorporating ceramic particles into a polymer may for example induce polymer degradation. Geary et al. describe (DOI: 10.1007/s10856-008-3472-8) that polycarbonate polyurethanes, like commercially available Bionate® grades, are suitable materials for use as in vivo biomedical devices, for example in replacing diseased or damaged joints. This Geary publication discloses incorporating hydroxyapatite (HA) particles in such polycarbonate polyurethanes via compounding. This bulk modification promotes degradation, resulting in significant reduction in molar mass of the polymer, and affects mechanical properties of the polymer material. In addition, the particles being dispersed throughout the polymer likely results in ceramic particles being fully covered by the polymer, and not being available at the surface for interaction with tissue or fluid after implantation.

The influence of polymer on surface exposure and osteoconductivity of bioceramic particles dispersed in a polymer was studied by Davison et al. (DOI: 10.1016/j.actbio.2012.04.007). Herein it was shown that when bioceramic particles are embedded and fully encapsulated in a polymeric binder that required a long time to dissolve in vitro and in vivo, the particles were not osteoconductive in a bone defect model, but rather were encapsulated by fibrous tissue formation. In contrast, using polymer compositions that easily dissolved or degraded promoted bone formation and bone bonding; explained by the bioceramic particles becoming exposed to the physiological environment.

An alternative approach toward making osteoconductive implants is surface modification of a polymer article or fiber, which has been extensively studied in last decades. Dorozhkin (DOI: 10.1016/j.msec.2015.05.033) reviewed in 2015 almost 1000 publications relating to methods of applying calcium phosphate ($CaPO_4$) deposits on implant materials, and concluded that, although it is generally accepted that $CaPO_4$-modification improves osteoconduction, further studies are needed to better understand bone responses to coated implant surfaces.

Li et al. (DOI: 10.1007/s00264-010-1158-6 and DOI: 10.1007/s00264-011-1275-x) described improved osseointegration of PET when provided with a hydroxyapatite/gelatin or bioactive glass/gelatin coating after plasma treatment. A subsequent surface treatment degrading gelatin of the coating is required to expose the ceramic particles, such that bone regeneration can occur. Furthermore, the use of bioderived gelatin presents some additional hurdles in terms of regulatory requirements and may introduce coating variability.

Li et al. (DOI: 10.1002/jbm.a.35218) in 2015 reviewed publications on various biomedical coatings on PET artificial ligaments and concluded that several coatings on PET, for example comprising hydroxyapatite, can increase bioactivity, but show several limitations, including bioceramic particle agglomeration and poor adhesion to PET substrates. Li et al. further concluded that complete characterization of critical factors is lacking and that further study to enhance osseointegration and biomechanical properties of coated grafts is needed.

Documents JP6339521A2 and JP6339522A2 described modification of fibers made from a bioinert material like UHMWPE, by first applying a LDPE coating having a lower melting point than the fiber itself, thermally softening this surface layer, and then spray coating with bioceramic particles. As the particles may be fully embedded in the polymer layer, plasma or chemical surface etching the surface layer is optionally applied to partly remove the polymer.

Publication US2011/0022085 describes the introduction of a biodegradable mineral layer onto suture material, preferably made of a biodegradable polymer, using a biomineralization process. In this process, the material surface is first functionalized with carboxylate anions, which serve as nucleation sites for a calcium- and phosphate-rich mineral layer during multi-day incubation in simulated body fluid (SBF), followed by exposure to a biological substance. The resulting bioactive suture material may be used as a vehicle for tissue healing and regeneration. Such mineralization process may be difficult to use on commercial scale, and the relatively thick mineral layer formed may be prone to mechanical delamination and disruption, with risk of particulate-induced inflammation.

In US 2016/0287242A1 an all-suture anchor is described, which anchor comprises a suture and a tubular sleeve that is composed of non-woven electrospun fibers. The fibers can be made from various degradable and non-degradable polymers, and may include a modifying agent, a biological agent or an antimicrobial agent. Preferably, the fibers have a diameter of 0.1-10 µm to encourage cellular attachment and tissue ingrowth and increase stability of the anchor in use. The modifying agent is indicated to include bioceramic particles providing osteoconductivity, but no actual compositions or anchors are described.

US2016/0144066A1 describes a method to prepare a bioactive all-suture anchor at the point of care, by dipping a fiber-based anchor in physiological fluid like blood from the patient and subsequently applying bioactive material by rolling or dipping the wetted anchor in bioceramic particles; producing the bioactive device at the time of surgery. Preferably bioactive glass particles of 5-500 µm are applied. This approach to making a bioceramic coating may suffer from a high degree of variability and poor particle bonding to the anchor, because the dip coating procedure is done during surgery and distribution of applied ceramic particles on the PET anchor may be poor. Such variability and low bioceramic homogeneity is mentioned in the above-referenced review by Li et al. Furthermore, the method requires manipulation immediately prior to or during surgery with the attendant infection risks of wet manipulation in the surgical theatre. In addition, the bioceramic particles will be only bound to a PET anchor through interactions with the body fluid, likely hampering improvement in stability of the implant.

SUMMARY

Despite numerous publications on methods of making fiber-based articles showing osteoconductive properties for use in a medical implant, including above cited documents, there is still a need in industry for a simple method to provide a fibrous polymer article with a bioactive surface that allows osseointegration after implantation like a bioceramic coating, while preserving the mechanical properties needed to function in its intended medical application. It is an object of present disclosure to provide such method and such fibrous polymer article.

The embodiments as described herein below and as characterized in the claims provide such method to make a fibrous article with a surface that shows enhanced bioactivity and allows osseointegration after implantation.

In accordance with an embodiment of the invention, a method of making a bioceramic coating on a fibrous article for use in a medical implant, comprises steps of
providing an article comprising fibers made from a biocompatible, non-biodegradable polymer;
coating at least the fibers that will be in contact with bone upon use as an implant with a solution of a coating polymer to result in coated fibers having a coating polymer layer;
treating the coated fibers with a dispersion of bioactive ceramic particles of particle size 0.01-10 µm in a treating solvent comprising a solvent for the coating polymer in at least one step; and
substantially removing the treating solvent;

to result in the particles being partly embedded in the coating polymer layer of the coated fibers; and as further defined by the claims.

The disclosed methods enable a relatively simple process to provide a complex shaped article like a fibrous article with a bioceramic coating, i.e. a coating comprising bioactive ceramic particles to result in a modified surface that shows bioactivity, especially osteoconductive properties, applying biocompatible compounds and mild conditions. The method can be used to modify fiber-based constructions used as a component of medical devices, and especially to provide a polyester fibrous article with a coating having bioactive inorganic particles like calcium phosphates to enhance bone growth on the article after implantation. The present coating method results in bioceramic particles at the surface of the fibers, which particles are exposed for interaction with their environment yet showing proper adhesion to the surface, and the method does not significantly affect mechanical properties of the fibrous article. The coated fibrous article thus obtained, for example, is found to show good initial pull-out strength from bone foam when used as sleeve component of a PET-based soft anchor, and to show biological activity in in vitro experiments.

Other embodiments of the invention thus concern a fibrous article showing bioactive properties, as obtainable with or obtained by the methods disclosed herein and comprising fibers with a bioceramic coating comprising a coating polymer and bioactive ceramic particles being partly embedded therein.

Further embodiments concern a method of making a medical implant, wherein the fibrous article as obtainable by or as obtained by the method as herein described is used as a component, and a medical implant thus obtained, especially a permanent high-strength orthopedic implant for repairing bone fractures or torn ligaments or tendons. Examples thereof include use in flexible tissue anchors, cortical fixation devices like ACL loops, high-strength orthopedic sutures, cerclage cables, synthetic tendon and ligament grafts, and interspinous spacers or spinal disc prostheses. Other embodiments include medical devices or implants comprising said fibrous articles.

BRIEF DESCRIPTION OF FIGURES

FIGS. 1A and 1B show optical pictures of PET film samples, coated with polyurethane and treated with HA dispersions in THF (Ex 1) and in water (CE 2) after staining with Alizarin red.

DETAILED DESCRIPTION OF EMBODIMENTS

Figure 2:
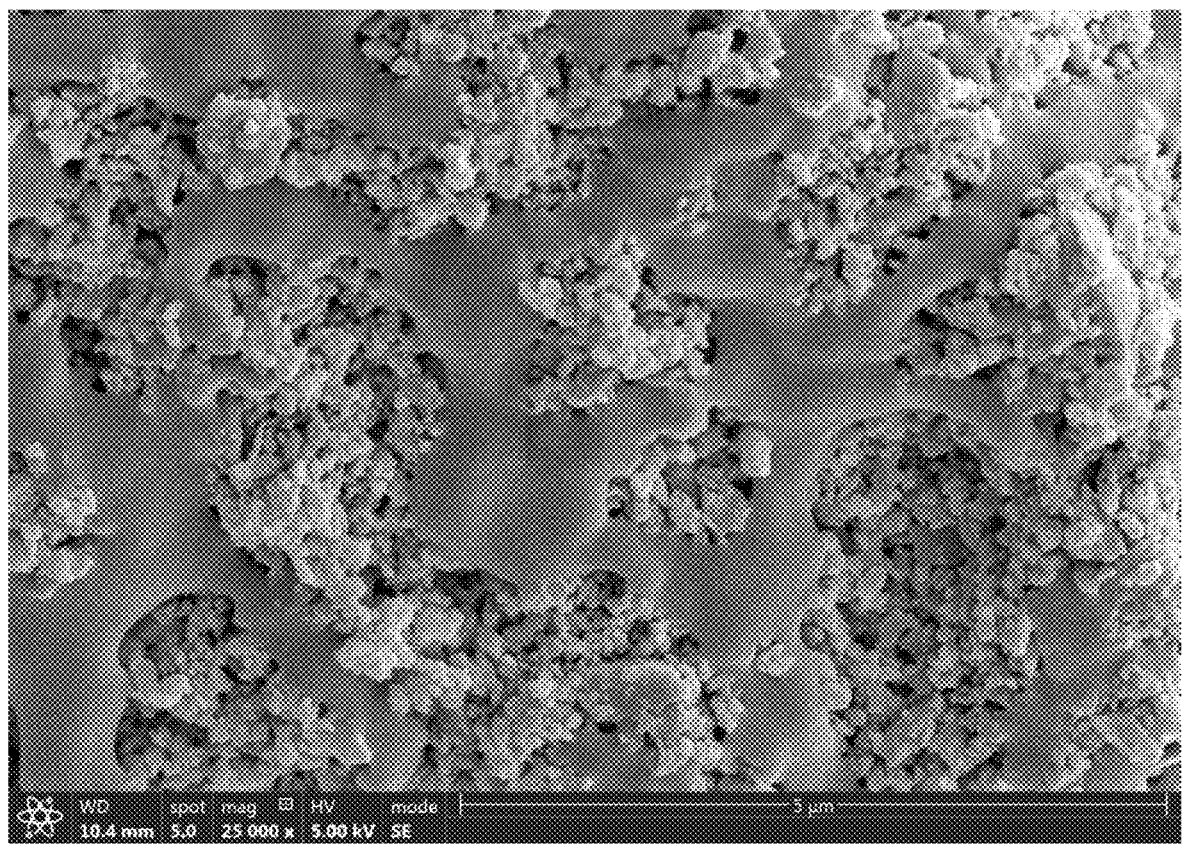
FIG. 2 shows a SEM micrograph of the surface of a PET fiber provided with a HA-comprising coating.
Figure 3A:
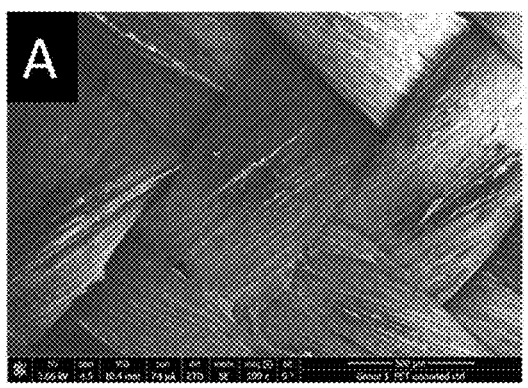
FIGS. 3A, 3B, 3C, 3D, 3E, 3F, 3G, and 3H show SEM micrographs of human mesenchymal stem cells cultured on braided PET (3A-3F) and HA discs (3G, 3H). (3A, 3B) are uncoated PET samples, PET coated with HA or HA/bTCP are shown in (3C, 3D) and (3E, 3F) respectively.
Figure 3B:
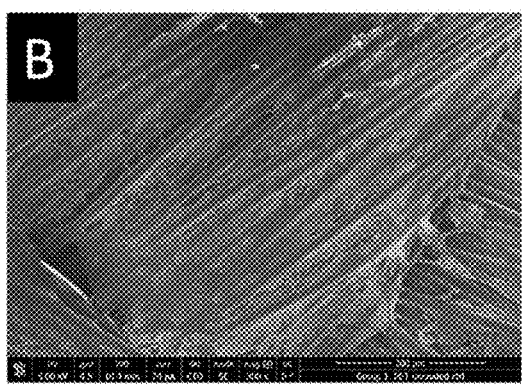
Figure 3C:
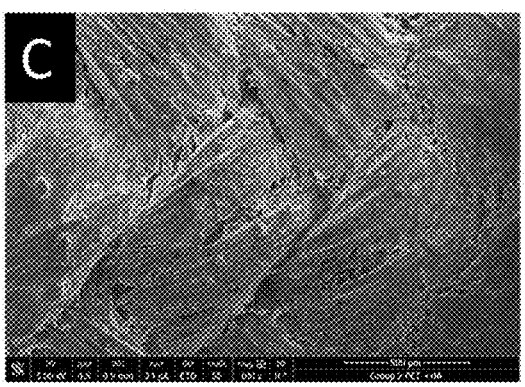
Figure 3D:
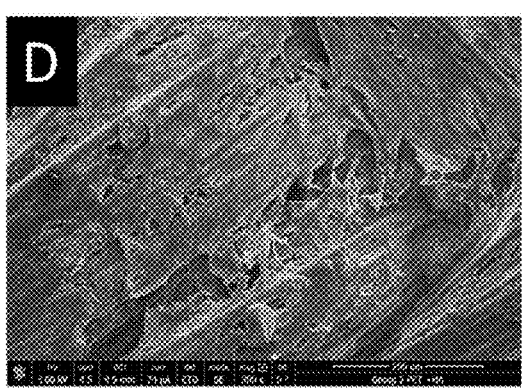
Figure 3E:
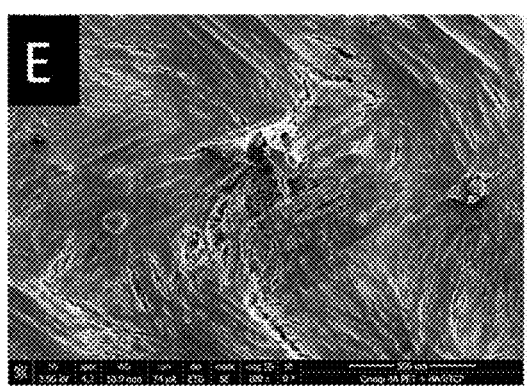
Figure 3F:
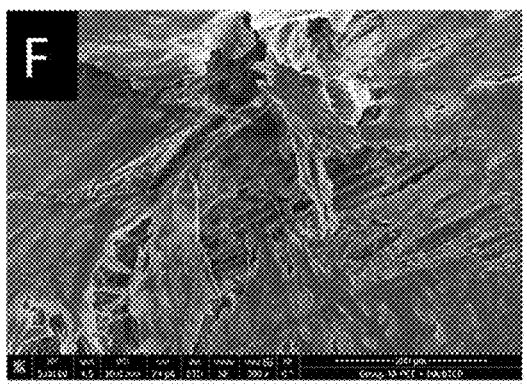
Figure 3G:
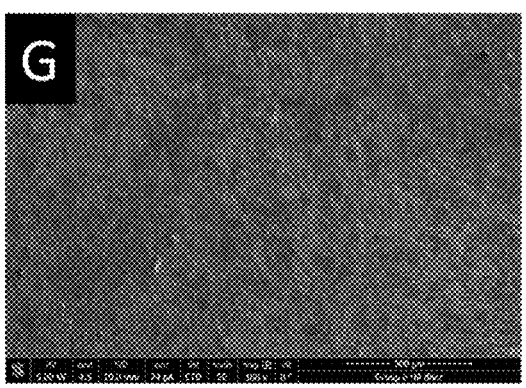
Figure 3H:
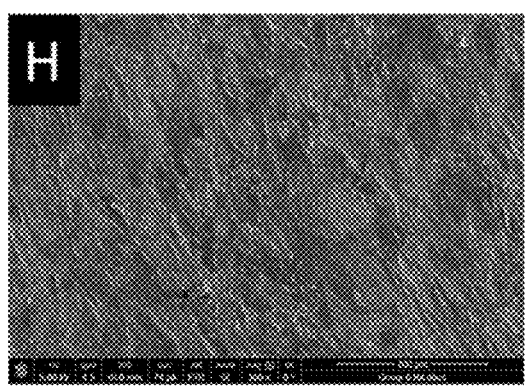

Within the context of present disclosures, a fibrous article is understood to mean an article comprising or substantially consisting of fibers, like braided, knitted or woven constructions, including sutures, cables and textiles or fabrics made from fibers or yarns. Fiber is a general name for a long continuous thread or filament, a yarn is a continuous strand of multiple generally twisted filaments. Braided, knitted or woven cables or fabrics are fibrous constructions made from at least one and generally multiple strands, wherein each strand can be at least one (mono)filament or a multifilament yarn.

A biocompatible material or compound herein means that the substance is biologically compatible by not producing a toxic, injurious, or immunologic response in living tissue. Biodegradable means a material is susceptible to chemical degradation or decomposition into simpler components by biological means, such as by an enzymatic or hydrolytic action under normal physiological conditions; and is also referred to as bio-resorbable. Biostable herein means a material is not biodegradable (also called non-biodegradable or non-bioresorbable).

Bioactivity is the ability of a material to elicit a specific biological response at the interface of the material and cells, body fluid or tissue, due to its reactive surface. In case of osteoconductivity, bioactivity results in growth of bony tissue onto the surface or into the porous structure of an implant or graft. Osseointegration refers to the formation of a direct interface between an implant and bone tissue, without intervening soft tissue, and resulting in mechanical anchorage of the implant; i.e., the functional result of an osteoconductive implant. Osteogenesis is formation of bone or development of bones, while osteoinduction refers to the act or process of stimulating osteogenesis.

A bioceramic coating is understood to mean a coating layer on a substrate surface comprising bioactive ceramic particles and showing bioactivity in contact with body fluid or tissue.

Although the following description is generally related to and illustrated with flexible tissue anchors and use thereof in tendon and ligament reconstruction, it will be understood that the methods and articles disclosed herein can also be applicable to other fiber-based devices and related surgical procedures wherein osseointegration plays a role, such as for example bone fracture repair and spinal applications.

In accordance with an embodiment of the invention, a method of making a bioceramic coating on a fibrous article for use in a medical implant, comprises steps of providing an article comprising fibers made from a biocompatible, non-biodegradable polymer;
  coating at least the fibers that will be in contact with bone upon use as an implant with a dispersion or solution of a coating polymer to result in coated fibers having a layer of coating polymer;
  treating the coated fibers with a dispersion of bioactive ceramic particles of particle size 0.01-10 µm in a treating solvent comprising a solvent for the coating polymer in at least one step; and
  substantially removing the treating solvent;
to result in the particles being partly embedded in the coating polymer layer of the coated fibers.

It may be true that Chetty et al. (DOI 10.1002/jbm.a.31465) describe an auricular implant that is made by coating a polyurethane article with a layer of hydroxyapatite (HA) via a 'solvent-compression method'. In this method, however, the article is coated by immersing in cyclohexanone to tackify the surface, making an assembly by placing the article between two layers of HA powder, placing the assembly in a die and compressing by applying a load, removing the assembly from the die and drying at elevated temperature, and extracting residual cyclohexanone with water. This process resulted in a HA coating layer with thickness of about 94 µm that adhered to the surface and showed bioactivity in in vitro testing. It is mentioned that thinner layers are difficult to achieve, whereas articles of complex shape would be difficult to coat with such compression method. Such method would thus not be applicable to a fibrous article. In addition, this publication does not describe or suggest a method comprising first applying a layer of a coating polymer on fibers, and then treating with a suspension of bioceramic particles in a solvent for said coating polymer without applying mechanical load.

Basically, with the methods disclosed herein a fiber-based article having a bioceramic coating is provided, the article comprising fibers with a coating layer having exposed ceramic particles adhered to it, and which article can be used as (a component of) an implant onto which bone tissue may grow. The article can be used in a medical implant, especially an orthopedic implant for use in orthopedic surgery concerning the musculosketetal system, which provides for form, stability and movement of the body. This system is made up of the body's bones (the skeleton), muscles, cartilage, tendons, ligaments, joints, and other connective tissue (the tissue that supports and binds tissues and organs together). The musculoskeletal system's primary functions include supporting the body, allowing motion, and protecting vital organs. The joints and musculoskeletal tissues of the human body may be subject to traumatic injury, disease and degenerative processes that over a period of time can lead to the deterioration or failure of a joint causing severe pain or immobility. Generally, the ability of a joint to provide pain free articulation and carry load is dependent upon the presence of healthy bone, cartilage and associated musculoskeletal tissues that provide a stable joint. In connection with present disclosure orthopedic surgery also relates to maintaining the motion in the various joints of the human body. Examples of orthopedic implants include bone anchors, plugs and screws, which are used in repairing bone fractures or torn ligaments and tendons, or in securing implants like artificial ligaments, tendons or cartilage replacement devices to bone.

In an embodiment, the method of making a bioceramic coating on a fibrous article for use in a medical implant, comprises a step of providing a fibrous article comprising fibers made from a biocompatible, non-biodegradable polymer; also referred to as a not bio-erodible or non-resorbable polymer. Suitable fibers have generally been made from a thermoplastic polymer, of which chemical composition may vary widely and mechanical properties, especially strength and modulus, are preferably in ranges compatible with, or matching those of bodily tissues like bone and ligaments. Biocompatible thermoplastic polymers that are used in fiber making include semi-synthetic and synthetic polymers. Semi-synthetic or bio-derived biocompatible polymers include materials like derivates of proteins and polysaccharides, such as cellulose. Synthetic biocompatible polymers include materials like poly(meth)acrylates, polyolefins, vinyl polymers, fluoropolymers, polyesters, polyamides, polysulfones, polyacrylics, polyacetals, polyimides, polycarbonates, polyurethanes, including copolymers, compounds and blends thereof. Such synthetic polymers may be based on natural compounds like amino acids and/or on synthetic monomers.

In a further embodiment, the biocompatible, non-biodegradable polymer is selected from polyolefins, polyketones, polyamides, and polyesters. Suitable polyolefins include polyethylenes and polypropylenes, especially such polymers of high molar mass like ultra-high molar mass polyethylene (UHMWPE). Suitable polyamides include aliphatic, semi-aromatic and aromatic polyamides, like polyamide 6, polyamide 66 and their copolymers, and poly(p-phenylene terephthalamide). Suitable polyesters include aliphatic, semi-aromatic and aromatic polyesters, like poly(l-lactic acid) and its copolymers, polyethylene terephthalate (PET), polytrimethylene terephthalate (PTT), polyethylene naphthalate (PEN), polyethylene furanoate (PEF) and liquid crystalline aromatic copolyesters. Polymer fibers can be made using different fiber spinning processes as known in the art; like solution spinning and melt spinning, including special techniques like gel spinning or electrospinning.

In an embodiment of present method, the fibrous article comprises fibers made from a polyethylene polymer, including homopolymer and copolymers. Copolymer polyethylene grades may comprise one or more other monomers to modify e.g. processing characteristics and physical properties, but generally in relatively low amount to preserve the semi-crystalline character of spun and drawn fibers that provide desired mechanical strength. In preferred embodiments, the fibrous article substantially consists of high molar mass polyethylene, like UHMWPE.

In another embodiment of present method, the fibrous article comprises fibers made from a polyalkylene terephthalate polymer like polyethylene terephthalate, including homopolymer and copolymers, in view of its properties profile and approved use in medical applications. Copolymer PET grades may comprise one or more other monomers to modify e.g. processing characteristics and properties, but generally in such amount that a semi-crystalline character of spun and drawn fibers is maintained. In preferred embodiments, the fibrous article substantially consists of polyalkylene terephthalate, like PET In the present method, the fibrous article may substantially consist of said fibers, but can also comprise other components. In case only a part of the article is made from fibers, the part that will be in contact with bone upon use in a medical implant comprises or substantially consists of said fibers. The article may have various different fiber constructions, like twisted, knitted, braided or woven constructs. The article—or fibrous part thereof—has such flexibility that allows it to be for example foldable, squashable, squeezable, deformable, soft, or elastic; for undergoing a change in shape during e.g. insertion into a bone tunnel and optionally further deformation to better fill the tunnel. In an aspect of the present disclosure, the fibrous article is a flexible tissue anchor, like a sleeve component and optionally a suture of the anchors described in U.S. Pat. No. 8,562,647B2 or US2016/0144066A1, and the article comprises at least braided fiber constructs.

In an embodiment, the present method optionally comprises a step of cleaning the article comprising fibers before the coating step, for example by applying at least one rinsing step to the fibers in order to remove any compounds potentially present that might negatively affect subsequent steps of the method or that would not comply with requirements for medical implants. Cleaning may be performed by rinsing with a single solution or solvent, but also with multiple solvents in sequential steps, wherein each subsequent rinsing step applies a solvent miscible with the solvent of the preceding step. Solvents of different polarities may thus be used, like a sequence ethanol-isopropanol-hexane-isopropanol-ethanol. Such cleaning step may also involve sonication. Multiple rinsing allows removal of potentially present compounds of different solubilities. The skilled person can select suitable cleaning solvents, depending on the situation. In an embodiment, the final rinsing is done with 96% ethanol.

In an embodiment, the present method optionally comprises a step of pretreating the article with a pre-wetting liquid, which may be a solvent or a non-solvent for the coating polymer that will be applied subsequently. Such pretreatment may be performed by submersing the article in the pre-wetting liquid, preferably followed by removing liquid from the surface and optionally outer region of the article, for example by evaporating liquid during a short time or by wiping the article surface with liquid absorbing material. The next step of coating with coating polymer will be done on the thus obtained pre-wetted article. Such pre-wetting step in present method limits or prevents penetration of the coating polymer through-out the fibrous article, resulting in an article wherein the coating polymer is mainly present on the surface and optionally in an outer region of the fibrous article. An advantage thereof is, that the coated fibrous article as obtained with the method retains much of its original flexibility. Suitable compounds for use as such pre-wetting liquid have enough affinity with the fiber polymer and fibrous article to penetrate and remain between the fibers of the article. Preferably, the pre-wetting liquid is a non-solvent for the fiber polymer so as not to deteriorate mechanical properties of the fibers in the article. The pre-wetting liquid may be the same as or different from the solvent for the coating polymer of the subsequent coating step.

The method according to present disclosure further comprises a step of coating at least the fibers that will be in contact with bone upon use as an implant with a solution or dispersion of a coating polymer.

In an embodiment, the method applies a dispersion of coating polymer, which comprises finely divided polymer particles in a non-solvent for the polymer, optionally prepared with an emulsifier or surfactant that is biocompatible. Preferably the non-solvent is an aqueous mixture or water. The person skilled in the art will be able to select suitable non-solvents and dispersion aids for a given coating polymer, or to select a commercially available dispersion that is suitable for use in present method based on present disclosures and his general knowledge, optionally supported by some literature and/or experiments.

In another embodiment, a solution of coating polymer is used for coating the fibers, which solution is made with a solvent wherein the polymer can be substantially, or preferably homogeneously dissolved. The person skilled in the art will be able to select a suitable solvent for a given coating polymer based on his general knowledge, optionally supported by some experiments and/or literature; for example on solubility parameters of solvents and polymers, like the "Polymer Handbook" by Brandrup and Immergut, Eds. The skilled person is also aware of effects of polymer molar mass on solubility. For a so-called good solvent for a polymer, interactions between polymer chain and solvent molecules are energetically favorable, and difference between solubility parameters of polymer and solvent is small. A solvent for a polymer can dissolve the polymer, for example assisted by stirring or sonication, and optionally by applying some heating. The solvent for the coating polymer preferably is not a good solvent, or even a non-solvent for the fiber polymer, so as not to deteriorate fiber properties. The concentration of coating polymer in the solution is not critical and may be chosen dependent on solubility and desired coating layer thickness. Generally, the concentration will be in the range 0.1-10 mass % of coating polymer in solvent. The solution contains e.g. at least 0.2, 0.5 or 1 mass %, and at most 8, 6, 4, 3 or 2 mass % of coating polymer.

In the present method, the step of coating the fibers with coating polymer can be performed in different ways. Based on the disclosure of the method and experiments herein, the skilled person will be able to select a suitable method and conditions to apply a layer of coating polymer; also depending whether a dispersion or solution of coating polymer is applied, and the solvent used. Suitable coating methods include dip coating and spray coating.

In an embodiment, the step of coating the fibers is performed at ambient conditions. Coating may also be performed at higher temperatures, depending on volatility of the dispersion non-solvent or solution solvent used. After applying the solution or dispersion of coating polymer, (non-) solvent is substantially removed by evaporation, if desired at elevated temperature to shorten time; to result in a layer of coating polymer on the fibers. In view of the subsequent steps of the method, solvent does not need to be completely removed at this stage, but a non-sticking surface layer is preferred to prevent treated fibers substantially adhering to each other.

In the present method, the step of coating the fibers results in fibers with a layer of coating polymer, the layer having a thickness that is sufficient to receive and partially embed the bioceramic particles in a subsequent step and will generally depend on particle sizes. For example, the thickness of the layer of coating polymer may be about half the size of the particles (taken as their d50 value, see hereinafter); so that the partially embedded particles still can protrude from the layer. In an embodiment of the method, the step of coating the fibers results in fibers having a layer of coating polymer of at least 0.05 µm thickness. In further embodiments, the layer thickness is at least 0.01, 0.05, 0.1, 0.2, 0.3, 0.4, 0.6, 0.8, or 1 µm; whereas the layer thickness generally does not need to be more than 50, 40, 40, 20, 10, 5, or 2 µm. A relatively thin coating layer will have little effect on properties like flexibility of the fiber construction of the article.

The thickness of the layer of coating polymer that is applied, in other words the amount of coating polymer, may also be defined by the relative mass increase of the article after coating. In embodiments of the present method, the mass increase upon coating the fibers of the article with coating polymer is at least about 0.1, 0.2, 0.3, 0.4, or 0.5 mass %, and at most about 3, 2.5, or 2 mass %.

A suitable coating polymer for use in this coating step of present method is biocompatible and compatible with the polymer from which the fibers are made, and preferably shows good adhesion to the fiber. The coating polymer is preferably non-biodegradable, and can be a homopolymer, (random) copolymer or block copolymer. The coating polymer may be thermosetting or thermoplastic, provided it can sufficiently be swollen or softened after coating during the treating step to result in partial embedding of bioceramic particles. The person skilled in the relevant art will be able to select a suitable coating polymer based on the directions provided in this disclosure in combination with general knowledge. For example, suitable combinations of fiber polymer and coating polymer may include combinations of biocompatible and non-biodegradable polymers such as UHMWPE with less crystalline or lower melting polyethylenes like LDPE; polyamide 66 with copolyamides or polyurethanes; and PET with copolyesters or polyurethanes.

In an embodiment of the method, the fibers are made from a polyamide or polyester and the coating polymer is a polyurethane. In a further embodiment, the fibers are made from PET and the coating polymer is a polyurethane.

In other embodiments of the present method, the coating polymer applied is a thermoplastic block copolymer. Block copolymers (or segmented) copolymers are polymers comprising blocks (also called segments) of polymers (including oligomers) that are chemically distinct, and that typically show different thermal and mechanical properties, and different solubilities. Often the blocks in a block copolymer comprising two (or more) types of blocks are referred to as being 'hard' and 'soft' polymer blocks, such different blocks resulting in microphase separation. The hard block in a block copolymer typically comprises a rigid or high modulus semi-crystalline or amorphous polymer, with—respectively—a melting temperature (Tm) or a glass transition temperature (Tg) higher than the use temperature, of e.g. about 35° C. The soft block in the block copolymer often comprises a flexible, amorphous polymer with a Tg lower than 35° C., preferably lower than 0° C. Thermal parameters like Tm and Tg are generally determined on dry samples; using well-known techniques like DSC or DMA. In such phase-separated block copolymers, the hard segments function as physical crosslinks for the flexible soft segments, resulting in materials having properties that may range from fairly stiff to flexible and elastic, depending on the ratio of hard to soft segments. When such block copolymer is heated above the softening point of the hard blocks, it will become a viscous fluid and may be processed into an article of desired shape and will solidify upon cooling. Such thermoplastic block copolymers showing flexibility or elastomeric character are generally referred to as thermoplastic elastomers, or TPEs.

In an embodiment, the coating polymer used in present method is a TPE material. The TPE comprises hard and soft blocks, wherein the hard block comprises a polymer chosen from the group consisting of polyesters, polyamides, polystyrenes, polyacrylates, polyurethanes and polyolefins; and the soft block comprises a polymer chosen from the group consisting of polyethers, polyesters, polyacrylates, polyolefins and polysiloxanes. Such polymers for the blocks are understood herein to include oligomers, homopolymers and copolymers, and polyesters are considered to include polycarbonates. Examples of TPE block copolymers are copolyester esters, copolyether esters, and copolycarbonate esters, wherein the hard blocks typically are based on semi-aromatic polyesters like polybutylene terephthalate (PBT); copolyester amides and copolyether amides; ethylene-propylene block copolymers; styrene-ethylene-butadiene block copolymers (SEBS); styrene-isobutylene block copolymers (SIBS); and polyurethanes comprising hard blocks based on diisocyanates and chain extenders, and polyester, polyether or polysiloxane soft blocks.

In further embodiments of the present inventions, a polyurethane, more specifically a polyurethane block copolymer or TPE, is applied as coating polymer. The term polyurethane denotes a family of polymers basically including three principle components; that are a polyol or macroglycol, a diisocyanate and a chain extender. Polyurethanes have a backbone that includes urethane groups and optionally also some urea groups in the repeating units of the polymer backbone, resulting from reaction of a diisocyanate with a diol and optionally a diamine as chain extender. Suitable diisocyanates include aromatic and aliphatic or cycloaliphatic compounds. Chain extenders are typically low molar mass aliphatic compounds, having two or more hydroxyl or amine groups. Bifunctional chain extenders result in linear, thermoplastic polymers, whereas multifunctional chain extenders lead to crosslinked, thermoset products. When also a polyol is used as diol, a block copolymer or TPE results, with the polyol as soft block and hard blocks formed by the urethane (and optionally urea) repeating units. Generally known polyurethane block copolymers and methods to prepare these copolymers are described in a.o. U.S. Pat. Nos. 4,739,013, 4,810,749, 5,133,742 and 5,229,431.

In embodiments of the present method, a polyurethane TPE (also referred to as TPU) is used as coating polymer, which comprises as soft block an aliphatic polyester diol, an aliphatic polyether diol, or a polysiloxane diol. As for chain extenders, also amine-functional soft blocks can be used, resulting in additional urea linkages. Biocompatibility and non-biodegradability (or biostability) of polyurethane block copolymers in the human body is proven. Mechanical and other properties of a polyurethane block copolymer can be tailored by varying chemical compositions and/or molar mass of the blocks. The hard blocks of a block copolymer for use in the method of the invention, including polyurethane TPE, may have a molar mass of about 160 to 10,000 Da, and more preferably about 200 to 2,000 Da. The molar mass of the soft segments may be typically about 200 to 100,000 Da, and preferably about 400 to 9000 Da. The ratio of soft to hard blocks can be chosen to result in certain stiffness or hardness of the polymer. Typically, durometer hardness of the polyurethane as measured with the Shore test using A or D scales, may be from 40 ShA, or at least 50 or 60 ShA and up to 80 or 75 ShD, generally representing a flexural modulus range of about 10 to 2000 MPa.

In further embodiments of present method, the polyurethane TPE comprises an aliphatic polyether or an aliphatic polyester as soft block, more specifically an aliphatic polycarbonate. Suitable polyethers include poly(propylene oxide)diols, poly(tetramethylene oxide)diols, and their copolymers. Suitable aliphatic polyesters are generally made from at least one aliphatic dicarboxylic acid and at least one aliphatic diol, which components are preferably chosen such that an essentially amorphous oligomer or polymer is formed having a Tg below 10, 0, or −10° C. Aliphatic polycarbonate diols are based on similar aliphatic diols as used for other polyester diols, and can be synthesized via different routes as known in the art. A suitable example is a poly(hexamethylene carbonate)diol. The hard blocks in such polyurethane TPEs are typically based on an aromatic diisocyanate like toluene diisocyanate, and a low molar mass aliphatic diol like 1,4-butanediol. A polycarbonate urethane or TPU may be suitably used for biomedical applications, in view of their flexibility, strength, biostability, biocompatibility and wear resistance. Commercially available examples of such polymers include the Bionate® PCU products (DSM Biomedical BV).

In an embodiment, the coating polymer used in the method may be a blend of two or more polymers and may further comprise one or more customary additives that are allowed for the targeted use of the article made. Examples of additives are anti-oxidants, processing aids, lubricants, surfactants, antistatic agents, colorants, radiopaque agents, and fillers. The additives may be present in the typically effective amounts as known in the art, such as 0.01-5 mass % based on the amount of the polymer, preferably 0.01-1 mass %. In another embodiment, the coating polymer substantially consists of polymer, and contains substantially no additives.

The method according to present disclosure further comprises a step of treating the coated fibers with a dispersion of bioactive ceramic particles of particle size 0.01-10 µm in a treating solvent that comprises a solvent for the coating polymer in at least one step. This step concerns a surface treatment of the coating polymer layer with a dispersion of bioactive ceramic particles in a treating solvent. Suitable bioactive ceramic particles for use in present methods include all inorganic materials that show the capability of direct bonding to living bone, for example by formation of biologically active bone-like apatite through chemical reaction of the particle surface with surrounding body fluid. Examples of suitable materials include various calcium phosphates and so-called bioactive glass or Bioglass®. Barrère et al. describe in Int. J. Nanomedicine 2006:1(3), 317-332 various suitable types of calcium phosphates, like dicalcium phosphate anhydrate ($CaHPO_4$; DCPA), dicalcium phosphate dihydrate ($CaHPO_4 \cdot 2H_2O$; DCPD), octacalcium phosphate ($Ca_8(HPO_4)_2 \cdot 5H_2O$; OCP), tricalcium phosphate ($Ca_3(PO_4)_2$; TCP), and hydroxyapatite ($Ca_{10}(PO_4)_6(OH)_2$; HA). Also blends of different types may be applied, or even show advantages; like certain mixtures of HA and TCP. The ceramic particles may in addition to their main constituents comprise small or trace amounts of other (inorganic) elements or ions, like Na, Mg, Fe, Zn, Ti, Ag, Cu or $—SO_4$, or $—CO_3$, which may improve specific properties of the particles. Bioactive glass or Bioglass®, which is also used as a trademark, refers to mixed organic oxides that have a surface-reactive glass film compatible with tissues; and may be used as a surface coating in some types of medical and dental implants. The Bioglass® 45S5 grade, for example, is indicated to be a glass composed of 45 mass % $SiO_2$, 24.5 mass % CaO, 24.5 mass % $Na_2O$, and 6.0 mass % $P_2O_5$. The high ratio of calcium to phosphorus in this material would promote formation of apatite crystals; calcium and silica ions can act as crystallization nuclei. Glasses are non-crystalline amorphous solids that are commonly composed of silica-based materials with minor of other inorganic elements.

In an embodiment, the bioactive ceramic particles have a particle size in the range 0.01-10 μm. Particle size and size distribution can be measured with SEM or optical microscopy, or with (laser) light diffraction techniques. Within present disclosure the d50 value as measured with light diffraction according to ISO 13320:2009, e.g with a Malvern Mastersizer 2000, is defined as the particle size of the bioceramic particles. The particle size does not appear to be specifically critical, but a dispersion of relatively small particles in a relatively low viscous solvent is easier to make and will show better stability than of particles of for example microsize range. Although larger particles have been mentioned in literature to be more effective in interacting with body fluid and cells, present method provides a bioactive article with particles smaller than 10 μm. In other embodiments of the present method, the ceramic particles having size of at least 50, 100, 200, 300, 400, or 500 nm are used. Further embodiments of the method use ceramic particles having size of at most 8, 7, 6, 5, 4, 3, 2 μm, or at most 1 μm.

The method comprises a surface treatment of the coating polymer layer with a dispersion of bioactive ceramic particles in a treating solvent comprising a solvent for the coating polymer. The person skilled in the art will be able to select a suitable solvent for a given coating polymer based on his general knowledge, optionally supported by some literature; for example on solubility parameters of solvents and polymers, like the "Polymer Handbook" by Brandrup and Immergut, Eds. For a so-called good solvent for a polymer, interactions between polymer chain and solvent molecules are energetically favorable, and difference between solubility parameter of polymer and solvent is small. A solvent for a coating polymer can substantially dissolve the polymer, optionally by applying some heating.

The solubility or maximum concentration of coating polymer in this treating solvent does not need to be high; a few mass % being dissolvable already represents a solvent for the coating polymer. The treating solvent may be a single solvent or a mixture of solvents, including good solvents for the coating polymer, less good solvents for the polymer, and non-solvents for the polymer, for reasons as further discussed hereafter. The treating solvent may be the same or different from the solvent used in making a solution of the coating polymer.

In an embodiment of the method, the treating solvent substantially or completely consists of a solvent for the coating polymer. This allows a relatively simple process, and short contacting times of the particles dispersion with the layer of coating polymer to effectively modify the surface.

In another embodiment, the treating solvent comprises a solvent for the coating polymer and a non-solvent for the coating polymer, wherein the solvents are miscible. It was observed that a good solvent for the polymer may, in addition to swelling a surface layer, also solubilize the layer; which may result in partial removal of the coated polymer, or in ceramic particles being completely enclosed or embedded by coating polymer. It has been surprisingly found that varying the composition of such treating solvent mixture, provides the skilled person with a tool to influence the degree of embedding of the ceramic particles in the layer of coating polymer on the fibers; to preferably result in particles that are partially embedded in coating polymer for good adhesion to the fibers, while not being fully covered with a polymer film and thus directly exposed with part of its surface to the environment and accessible for interaction with body fluid after implantation. The skilled person can find proper solvent combinations for the treating solvent and a selected coating polymer, based on his knowledge and with some experimental work. Preferably, the non-solvent has a lower boiling point, that is higher rate of evaporation, than the solvent for the coating polymer. Without wishing to be bound to any theory, the inventors reason that upon evaporation of non-solvent a relatively small amount of solvent for the coating polymer remains at the surface, which results in a swollen surface layer and the particles partly sinking into and becoming partly embedded in the solvent-swollen coating polymer surface. In this respect, it is noted that a treating solvent mixture that is not a solvent for the polymer as such, will only result in particles being embedded if a solvent composition that is able to swell the coating polymer surface is formed during the process at the surface of the coated fibers, e.g. by evaporation of non-solvent from the composition. Using a dispersion in a non-solvent for the coating polymer can without the embedding still result in particles being physically entrapped between filaments of the fibrous construction, but without being adhered to the fibers. The treating solvent may comprise a solvent and a non-solvent for the coating polymer in widely varying ranges, like 98-2 vol % of solvent for the coating polymer, or at most 90, 80, 70, 70, 60, 50, 40, 30, 20, 10, 5 or at most 2 vol % of solvent for the coating polymer, based on total mass of treating solvent.

In embodiments of the method, for example, wherein the coating polymer is a polyurethane, or a polyurethane block copolymer, the treating solvent comprises as solvents for the coating polymer compounds like tetrahydrofuran (THF), methyl-tetrahydrofuran (m-THF), dimethylformamide (DMF), dimethylacetamide (DMAc), dimethylsulfoxide (DMSO), dioxane, dioxolane, or mixtures thereof. Suitable non-solvents for use in the treating solvent include for example lower aliphatic alcohols like ethanol, aliphatic esters, aliphatic ethers, and lower alkanes and alkenes. As indicated above, the non-solvent can preferentially evaporate from a mixture forming the treating solvent during the method. In embodiments of the method, the first solvent substantially consists of solvent and optionally non-solvent for the polymer.

In embodiments of the method, the particle dispersion in a treating solvent comprises 1-25 mass % of bioactive ceramic particles. It was found that a relatively high concentration of particles in the dispersion may result in high surface coverage, but may have disadvantages of high viscosity, dispersion instability, or non-homogeneous coating and surface coverage. Therefore, use of dispersions comprising at most 22, 20, 18, 16, 14, 12 or 10 mass % of ceramic particles is preferred. As very low particle concentrations result in low surface coverage, the dispersion used preferably comprises at least 2, 3, or 5 mass % of ceramic particles.

In embodiments of the present method, a dispersion of bioactive ceramic particles in a treating solvent is made using known means. For example, a dispersion is made using mechanical stirring means, such as by applying high speed and/or high shear stirring and optionally sonication; preferably the dispersion is substantially free of additives like dispersion aids or surfactants. This has the advantage that the fibrous article made will also not comprise such additives, although the dispersion may show some settlement caused by density difference of ceramic particles and treating solvent. For this last reason, the dispersion is typically being stirred until shortly before using the dispersion to treat the coated fibers.

In another embodiment of the present method, a dispersion of bioactive ceramic particles in a treating solvent is made by mechanical means, for example by applying high speed and/or high shear stirring and optionally sonication, with addition of effective amounts of biocompatible additives like dispersion aids or surfactants to better disperse the particles and to stabilize the dispersion thus made.

In further embodiments, sonication is applied before and/or during making a ceramic particle dispersion to help disaggregation of possibly present aggregates of particles and their dispersion in treating solvent.

The method of making a bioceramic coating on a fibrous article for use in a medical implant further comprises treating the coated fibers with a dispersion of bioactive ceramic particles in a treating solvent in at least one step. Different ways of treating the coated fibers, involving contacting the surface of the coated fibers with the particles dispersion during a relatively short time, can be applied in present method. Based on the disclosure of the method and experiments herein, the skilled person will be able to select a suitable method and conditions that will result in particles becoming partly embedded in the coating polymer layer; also depending on type of coating polymer and the treating solvent used. Suitable treating methods include dip coating and spray coating to contact the coated fibers with the dispersion. Such coating methods allow to apply a thin layer of the dispersion on the surface of a complex shaped article like a fibrous article within short time, optionally using multiple coating steps with intermediate drying, and with controllable contact time of coating polymer and dispersion, before removing excess dispersion and/or removing at least part of the treating solvent, e.g. by drying/evaporating and/or by rinsing with a rinsing solvent. Treating can be suitable performed at ambient conditions, but for example the temperature may also be increased, e.g. to shorten contacting and subsequent drying times.

In an embodiment of the method, treating is done by dip coating the fibrous article comprising coated fibers with the bioceramics dispersion in at least one step. To prevent particles becoming fully embedded in the coating polymer, treating time is preferably kept short. Suitable time for a dip coating step, that is the time the article is submerged in the dispersion, include periods of 1-20 s. By applying multiple short dip coating steps it appeared possibly to better control coverage of the surface with ceramic particles, rather than aiming to obtain a certain coverage in one step. In preferred embodiments therefore, the method comprises at least 2, 3, 4, 5, 6, 7, 8, 9 or dip coating steps, optionally using intermediate drying periods to remove at least part of the treating solvent. A drying period can vary from 1 to 10 min, depending of conditions and volatility of treating solvent (or solvents contained therein). Suitable temperatures for coating and drying are in the range 10 to 150° C., a.o. depending on the softening temperature of the fibers of the article; and is typically about 40-60° C., optionally in combination with reduced pressure and/or inert gas, like nitrogen flow.

In further embodiments, treating with bioceramic particles dispersion may be done multiple steps, applying different dispersions; that is dispersions comprising different bioceramic particles. The particles may for example differ in their chemical composition, and/or in particle size. In case bioceramic particles of different size are used, the dispersion having largest particles is preferably used first, and smallest particles are used in a last treating step. Such multi-step approach may result in more effective surface coverage, while also resulting in smaller particles being exposed on the surface.

In embodiments wherein spray coating is used, applying multiple thin layers with preferably intermediate drying may also be advantageous over applying one thick coating layer, for similar reasons as mentioned above for dip coating. The amount of bioceramic particles in the layer of coating polymer that result from the treating step, may be defined by the relative mass increase of the coated article after the treatment. In embodiments of the present method, the mass increase of the coated fibrous article upon treating with bioceramics dispersion, after removing the treating solvent, is at least about 0.1, 0.2, 0.3, 0.4, or 0.5 mass %, and at most about 20, 17, 15, 12, 10, 7, 5, 4, 3, 2.5, or 2 mass %.

The method of making a bioceramic coating on a fibrous article for use in a medical implant further comprises a step of substantially removing the treating solvent. In embodiments of the method this is done by evaporating or drying. Drying conditions are dependent on volatilities of components to be removed, and the skilled person can determine suitable conditions. Drying can be done at ambient conditions, but also at elevated temperatures, under reduced pressure and/or by applying an inert gas flow.

In other embodiments, the method may alternatively (or optionally) comprise a step of rinsing the coated and treated fibers with a rinsing solvent being a non-solvent for the polymer. This rinsing step aims to completely remove residual treating solvent and possible other compounds, to make an article that will comply with requirements for medical implants. Treating the modified fibers with non-solvent for the coating polymer may also further stabilize the morphology obtained, as the coating polymer surface layer is no longer swollen by solvent. Rinsing may be performed with a single rinsing solvent, but also with multiple rinsing solvents in sequential steps, wherein the first rinsing solvent applied is miscible with the treating solvent, and each subsequent rinsing applies a rinsing solvent miscible with the preceding rinsing solvent. A rinsing solvent may consist of a single solvent but may also comprise a mixture of compounds. Rinsing solvent of different polarities may thus be used, like a sequence ethanol-isopropanol-hexane-isopropanol-ethanol. This multiple rinsing allows removal of potentially present compounds of different solubilities. The skilled person can select suitable rinsing solvents, including non-solvents for the polymer as described above, depending on the situation. In an embodiment, the final rinsing is done with 96% ethanol.

The method of making a bioceramic coating on a fibrous article for use in a medical implant results in bioactive ceramic particles present at the surface of coated fibers of the article, which particles are partly embedded in polymer of said coating. In addition, the method does not deteriorate, or only slightly affects mechanical properties of the fibrous article. The resulting partially embedded particles properly adhere to the surface, yet they are exposed at the surface; that is, they are accessible for direct interaction their environment, especially with body fluid or tissue after implantation. Stated otherwise, the ceramic particles are not covered by a thin polymer layer that would prevent such direct interaction. The fibrous article showing osteoconductive properties made with the present method is furthermore found to show good initial pull-out strength from bone foam, for example when used as sleeve component of a PET-based soft anchor, and to show biological activity in in vitro and in vivo experiments.

In other embodiments, therefore, the present disclosure provides an osteoconductive fibrous article for use as an orthopedic implant or a component thereof, as obtainable by or as obtained by the method as herein described. This osteoconductive fibrous article shows properties as described hereinabove for the method of making the article, including any combination of features; unless such combination would be clearly physically impossible.

In accordance with a further embodiment, an osteoconductive fibrous article for use as (a component of) an orthopedic implant is provided, which article comprises biocompatible, non-biodegradable polymer fibers, which fibers have a coating layer comprising a coating polymer and bioactive ceramic particles of particle size of 0.01-10 μm, which particles are partly embedded in the coating polymer. The fibrous article comprises bioactive particles adhering to the surface that are accessible for interaction with surrounding tissue or fluid when used as an implant. This osteoconductive fibrous article shows all properties as described hereinabove for the method of making the article, including any combination of features; unless such combination would be clearly physically impossible.

In another embodiment, the present disclosure relates to the use of the osteoconductive fibrous article as obtainable by or as obtained by the method as herein described as a component of a medical implant or as a medical implant.

In another embodiment, the present disclosure relates to the use as a component of a medical implant or as a medical implant of an osteoconductive fibrous article that comprises biocompatible, non-biodegradable polymer fibers, which fibers have a coating layer comprising a coating polymer and bioactive ceramic particles of particle size of 0.01-10 μm, which particles are partly embedded in the coating polymer.

In another embodiment, the present disclosure relates to a method of making a medical implant, wherein the osteoconductive fibrous article as obtainable by or as obtained by the method as herein described is used as a component of the medical implant.

In another embodiment, the present disclosure relates to a method of making a medical implant, wherein an osteoconductive fibrous article that comprises biocompatible, non-biodegradable polymer fibers, which fibers have a coating layer comprising a coating polymer and bioactive ceramic particles of particle size of 0.01-10 μm, which particles are partly embedded in the coating polymer is used as a component of the medical implant.

In another embodiment, the present disclosure relates to a medical implant comprising the osteoconductive fibrous article as obtainable by or as obtained by the method as herein described.

Examples of a medical implant include permanent high-strength orthopedic implants for repairing bone fractures or torn ligaments or tendons; like flexible tissue anchors, cortical fixation devices like ACL loops, high-strength orthopedic sutures, bone cerclage cables, synthetic tendon and ligament grafts, interspinous spacers or spinal disc prostheses, spinal fusion devices, or synthetic scaffolds to repair bone voids. A flexible tissue anchor is a device for anchoring a suture to a bone and can be applied to attach or secure soft tissue to a bone, to attach or secure bone to bone, or to attach or secure bone to structures. Non-limiting examples of soft tissue include tendons, ligaments, fascia, skin, fibrous tissues, synovial membranes, fat, muscles, nerves, and blood vessels.

In further embodiments, the present disclosure relates to medical devices or implants as described above, comprising said fibrous articles, especially as the part of the device or implant that will interface with bone.

Any one of the embodiments, aspects and preferred features or ranges as disclosed in this application may be combined in any combination, unless stated otherwise herein or if technically clearly not feasible to a skilled person. Various aspects of the invention are further summarized in the below set of embodiments.

101. A method of making a bioceramic coating on a fibrous article for use in a medical implant, comprising steps of
   providing an article comprising fibers made from a biocompatible, non-biodegradable fiber polymer;
   coating at least the fibers that will be in contact with bone upon use as an implant with a dispersion or solution of a coating polymer to result in coated fibers having a layer of coating polymer;
   treating the coated fibers with a dispersion of bioactive ceramic particles of particle size 0.01-10 μm in a treating solvent comprising a solvent for the coating polymer in at least one step; and
   substantially removing the treating solvent;
   to result in the particles being partly embedded in the coating polymer layer of the coated fibers.
102. The method of embodiment 101, wherein the biocompatible thermoplastic polymer is a semi-synthetic or a synthetic polymer.
103. The method of embodiment 101 or 102, wherein the synthetic biocompatible polymer is at least one selected from the group consisting of poly(meth)acrylates, polyolefins, vinyl polymers, fluoropolymers, polyesters, polyamides, polysulfones, polyacrylics, polyacetals, polyimides, polycarbonates, polyurethanes, and copolymers and compounds thereof)
104. The method of anyone of embodiments 101-103, wherein the biocompatible, non-biodegradable polymer is at least one selected from the group consisting of polyolefins, polyketones, polyamides, and polyesters.

105. The method of anyone of embodiments 101-104, wherein the biocompatible, non-biodegradable polymer is a polyethylene or a polypropylene, preferably of high molar mass.
106. The method of embodiment 105, wherein the polymer is a polyethylene, including homopolymer and copolymers.
107. The method of anyone of embodiments 101-106, wherein the fibrous article substantially consists of high molar mass polyethylene, preferably of UHMWPE.
108. The method of embodiment 101 or 102, wherein the biocompatible, non-biodegradable polymer is an aliphatic, semi-aromatic or aromatic polyamide, like polyamide 6, polyamide 66 and their copolymers, or poly(p-phenylene terephthalamide).
109. The method of embodiment 101 or 102, wherein the biocompatible, non-biodegradable polymer is an aliphatic, semi-aromatic or aromatic polyester, like poly (L-lactic acid), polyethylene terephthalate (PET), polytrimethylene terephthalate (PTT), polyethylene naphthalate (PEN), polyethylene furanoate (PEF) or a liquid crystalline aromatic copolyester. 110. The method of embodiment 109, wherein the polyester is a polyalkylene terephthalate, preferably from polyethylene terephthalate, including homopolymer and copolymers,
111. The method of anyone of embodiments 101-110, wherein the fibrous article substantially consists of a polyester, preferably of PET.
112. The method of any one of embodiments 101-111, wherein the fibers have been made using solution spinning, melt spinning, gel spinning or electrospinning.
113. The method of any one of embodiments 101-112, wherein a part of the fibrous article that will be in contact with bone upon use in a medical implant comprises or substantially consists of fibers.
114. The method of any one of embodiments 101-113, wherein the article or at least a fibrous part thereof is of a twisted, knitted, braided or woven fiber construction.
115. The method of embodiment 114, wherein the article comprises at least braided fiber construct.
116. The method of embodiment of any one of embodiments 101-114, wherein the fibrous article is a flexible tissue anchor, or a sleeve component thereof.
117. The method of anyone of embodiments 101-116, further comprising a step of cleaning the article comprising fibers before the coating step, preferably by applying at least one rinsing step to the fibers to remove any compounds potentially present that might negatively affect subsequent steps of the method or that would not comply with requirements for medical implants.
118. The method of embodiment 117, wherein cleaning is performed by rinsing with a single solution or solvent.
119. The method of embodiment 117, wherein cleaning is performed by rinsing with multiple solvents in sequential steps, wherein each subsequent rinsing step applies a solvent miscible with the solvent of the preceding step.
120. The method of embodiment 119, wherein cleaning is performed in sequential steps using ethanol-isopropanol-hexane-isopropanol-ethanol.
121. The method of anyone of embodiments 119-120, wherein a final rinsing step is done with 96% ethanol.
122. The method of anyone of embodiments 117-121, wherein cleaning comprises sonication.
123. The method of anyone of embodiments 101-122, further comprising a step of pretreating the article with a pre-wetting liquid, optionally followed by removing excess liquid from the surface and optionally from an outer region of the article.
124. The method of anyone of embodiments 101-123, wherein the coating is done with a dispersion of coating polymer, which comprises finely divided polymer particles in a non-solvent for the coating polymer, is used, optionally prepared with a biocompatible emulsifier or surfactant.
125. The method of embodiment 124, wherein the non-solvent is an aqueous mixture or water.
126. The method of anyone of embodiments 101-123, wherein the coating is done with a solution of coating polymer, which solution is made with a solvent wherein the coating polymer can be substantially, or preferably homogeneously dissolved.
127. The method of embodiment 126, wherein the solvent for the coating polymer is not a good solvent for the fiber polymer, preferably a non-solvent for the fiber polymer.
128. The method of embodiment 126 or 127, wherein the solution of coating polymer has a concentration of 0.1-10 mass % of coating polymer in solvent, preferably at least 0.2, 0.5 or 1 mass % and at most 8, 6, 4, 3 or 2 mass % of coating polymer.
129. The method of anyone of embodiments 124-128, wherein the step of coating the fibers with coating polymer is performed by dip coating or spray coating.
130. The method of anyone of embodiments 124-129, wherein after applying the solution or dispersion of coating polymer, (non-)solvent is substantially removed by evaporation, optionally at elevated temperature, to result in a layer of coating polymer on the fibers preferably with a non-sticking surface.
131. The method of anyone of embodiments 124-130, wherein coating the fibers results in fibers having a layer of coating polymer of at least 0.05 µm thickness, preferably of at least 0.01, 0.05, 0.1, 0.2, 0.3, 0.4, 0.6, 0.8, or 1 µm; and thickness of at most of 50, 40, 40, 20, 10, 5, or 2 µm.
132. The method of anyone of embodiments 124-131, wherein a mass increase upon coating the fibers of the article with coating polymer is at least about 0.1 mass %, preferably at least 0.2, 0.3, 0.4, or 0.5 mass %, and at most 3 mass %, preferably at most 2.5, or 2 mass %.
133. The method of anyone of embodiments 124-132, wherein the coating polymer is a non-biodegradable homopolymer, (random) copolymer or block copolymer.
134. The method of anyone of embodiments 124-133, wherein the coating polymer is thermosetting or thermoplastic, which polymer can be swollen or softened after coating during the treating step to result in partial embedding of bioceramic particles.
135. The method of anyone of embodiments 101-134, wherein the fiber polymer is UHMWPE and the coating polymer a LDPE.
136. The method anyone of embodiments 101-134, wherein the fiber polymer is polyamide 66 and the coating polymer a copolyamide or a polyurethane.
137. The method of anyone of embodiments 101-134, wherein the fiber polymer is a polyalkylene terephthalate and the coating polymer a copolyester or a polyurethane.

138. The method of embodiment 137, wherein the fiber polymer is PET and the coating polymer a polyurethane.

139. The method of anyone of embodiments 101-134, wherein the coating polymer is a thermoplastic block copolymer, preferably comprising two or more types of blocks.

140. The method of embodiment 139, wherein the block copolymer comprises a hard block of a rigid or high modulus semi-crystalline or amorphous polymer, preferably with a melting temperature (Tm) or a glass transition temperature (Tg) higher than the use temperature, preferably of at least 35° C.

141. The method of embodiment 139 or 140, wherein the block copolymer comprises a soft block of a flexible, amorphous polymer with a Tg lower than 35° C., preferably lower than 0° C., or TPEs.

142. The method of anyone of embodiments 101-141, wherein the coating polymer is a thermoplastic elastomer (TPE).

143. The method of embodiment 142, wherein the TPE comprises hard block comprising a polymer chosen from the group consisting of polyesters, polyamides, polystyrenes, polyacrylates, polyurethanes and polyolefins, and soft block comprising a polymer chosen from the group consisting of polyethers, polyesters, polyacrylates, polyolefins and polysiloxanes.

144. The method of embodiment 142 or 143, wherein the TPE is selected from the group consisting of copolyester esters, copolyether esters, copolycarbonate esters, copolyester amides, copolyether amides, ethylene-propylene block copolymers, styrene-ethylene-butadiene block copolymers (SEBS), styrene-isobutylene block copolymers (SIBS), and polyurethanes comprising hard blocks based on diisocyanates and chain extenders, and soft blocks based on polyesters, polyethers or polysiloxanes.

145. The method of embodiment 142 or 143, wherein the coating polymer is a polyurethane block copolymer, which preferably comprises as soft block an aliphatic polyester diol, an aliphatic polyether diol, or a polysiloxane diol.

146. The method of embodiment 145, wherein the hard blocks have a molar mass of 160 to 10,000 Da, preferably 200 to 2,000 Da.

147. The method of embodiment 145 or 146, wherein the soft blocks have a molar mass of 200 to 100,000 Da, and preferably 400 to 9000 Da.

148. The method of anyone of embodiments 145-147, wherein the polyurethane has a durometer hardness as measured with the Shore test of at least 40 ShA, preferably at least 50 or 60 ShA and of at most 80 ShD, preferably at most 75 ShD.

149. The method of anyone of embodiments 145-148, wherein the polyurethane has a flexural modulus of 10 to 2000 MPa.

150. The method of anyone of embodiments 145-149, wherein the polyurethane comprises an aliphatic polyether or an aliphatic polyester as soft block, preferably an aliphatic polycarbonate, like a poly(hexamethylene carbonate)diol.

151. The method of anyone of embodiments 145-149, wherein the polyurethane comprises hard blocks based on an aromatic diisocyanate and a low molar mass aliphatic diol, preferably based on toluene diisocyanate and 1,4-butanediol.

152. The method of anyone of embodiments 101-151, wherein the coating polymer comprises at least one polymer and one or more customary additives, preferably at least one additive selected from anti-oxidants, processing aids, lubricants, surfactants, antistatic agents, colorants, radiopaque agents, and fillers.

153. The method of embodiment 152, wherein the at least one additive is present in an amount of 0.01-5 mass % based on the amount of the polymer, preferably 0.01-1 mass %.

154. The method of anyone of embodiments 101-151, wherein the coating polymer substantially consists of at least one polymer and contains substantially no additives.

155. The method of anyone of embodiments 101-154, wherein the bioactive ceramic particles are calcium phosphate or bioactive glass particles, preferably one or more type of particles selected from the group consisting of dicalcium phosphate anhydrate ($CaHPO_4$; DCPA), dicalcium phosphate dihydrate ($CaHPO_4 \cdot 2H_2O$; DCPD), octacalcium phosphate ($Ca_8(HPO_4)_2 \cdot 5H_2O$; OCP), tricalcium phosphate ($Ca_3(PO_4)_2$; TCP), hydroxyapatite ($Ca_{10}(PO_4)_6(OH)_2$; HA) and bioactive glass, more preferably a mixture of HA and bioactive glass particles.

156. The method of embodiment 155, wherein the bioactive ceramic particles comprise a bioactive glass composed of 45 mass % $SiO_2$, 24.5 mass % CaO, 24.5 mass % $Na_2O$, and 6.0 mass % $P_2O_5$.

157. The method of anyone of embodiments 101-156, wherein the bioactive ceramic particles have a particle size in the range 0.01-10 μm, with particle size measured as d50 with light diffraction according to ISO 13320:2009.

158. The method of embodiment 157, wherein the ceramic particles have size of at least 50, 100, 200, 300, 400, or 500 nm, and of at most 8, 7, 6, 5, 4, 3, 2 μm, or at most 1 μm.

159. The method of anyone of embodiments 101-158, wherein the treating solvent is a single solvent or a mixture of solvents, including good solvents for the coating polymer, less good solvents for the polymer, and non-solvents for the polymer.

160. The method of embodiment 159, wherein the treating solvent substantially or completely consists of a solvent for the coating polymer.

161. The method of embodiment 159, wherein the treating solvent comprises a solvent for the coating polymer and a non-solvent for the coating polymer, and the solvents are miscible 162. The method of embodiments 159 or 161, wherein the non-solvent has a higher rate of evaporation than the solvent for the coating polymer.

163. The method of anyone of embodiments 159, 161 and 162, wherein the treating solvent comprises 98-2 vol % of solvent for the coating polymer, preferably at most 90, 80, 70, 70, 60, 50, 40, 30, 20, 10, 5 or at most 2 vol % of solvent for the coating polymer, based on total mass of treating solvent.

164. The method of anyone of embodiments 101-163, wherein the coating polymer is a polyurethane or a polyurethane block copolymer, the treating solvent comprises as solvents for the coating polymer tetrahydrofuran (THF), methyl-tetrahydrofuran (m-THF), dimethylformamide (DMF), dimethylacetamide (DMAc), dimethylsulfoxide (DMSO), dioxane, dioxolane, or mixtures thereof, and the optional non-solvent comprises a lower aliphatic alcohols like ethanol, aliphatic esters, aliphatic ethers, or a lower alkane and alkene.
165. The method of anyone of embodiments 101-164, wherein the particle dispersion in a treating solvent comprises at most 22, preferably at most 20, 18, 16, 14, 12 or 10 mass % of ceramic particles, and at least 2, preferably at least 3, or 5 mass % of ceramic particles.
166. The method of anyone of embodiments 101-165, wherein the dispersion is made using mechanical stirring means, such as by applying high speed and/or high shear stirring and optionally sonication, and the dispersion is substantially free of additives like dispersion aids or surfactants.
167. The method of anyone of embodiments 101-165, wherein the dispersion is made by mechanical means, for example by applying high speed and/or high shear stirring and optionally sonication, with addition of effective amounts of biocompatible additives like dispersion aids or surfactants.
168. The method of anyone of embodiments 101-167, wherein treating the coated fibers is done by dip coating or spray coating, preferably using multiple coating steps with intermediate drying.
169. The method of anyone of embodiments 101-167, wherein treating the coated fibers comprises at least 2, preferably at least 3, 4, 5, 6, 7, 8, 9 or 10 dip coating steps, optionally using intermediate drying periods to remove at least part of the treating solvent.
170. The method of anyone of embodiments 101-169, wherein treating with a bioceramic particles dispersion is done in multiple steps applying different dispersions comprising different bioceramic particles.
171. The method of anyone of embodiments 101-170, wherein the mass increase of the coated fibrous article upon treating with bioceramics dispersion and after removing the treating solvent, is at least 0.1 mass %, preferably at least 0.2, 0.3, 0.4, or 0.5 mass %, and at most 20 mass %, preferably at most 15, 12, 10, 7, 5, 4, 3, 2.5, or 2 mass %.
172. The method of anyone of embodiments 101-171, further comprising a step of substantially removing the treating solvent.
173. The method of embodiment 172, comprising a step of rinsing the coated and treated fibers with a rinsing solvent being a non-solvent for the fiber and coating polymers, preferably with multiple rinsing solvents in sequential steps, wherein a first rinsing solvent applied is miscible with the treating solvent, and each subsequent rinsing applies a rinsing solvent miscible with the preceding rinsing solvent.
174. The method of embodiment 172 or 173, wherein rinsing solvents of different polarities are used, preferably a final rinsing is done with 96% ethanol.
201. A bioactive fibrous article for use as an orthopedic implant or as a component thereof, as obtainable by or as obtained by the method of anyone of embodiments 101-174.
202. A bioactive fibrous article for use as an orthopedic implant or as a component thereof, which article comprises biocompatible, non-biodegradable polymer fibers, which fibers have a coating layer comprising a coating polymer and bioactive ceramic particles of particle size of 0.01-10 μm, which particles are partly embedded in the coating polymer, and which article optionally has features as described in anyone of embodiments 102-174.
203. The bioactive fibrous article of embodiment 201 or 202, showing osteoconductive properties.
204. Use of the bioactive fibrous article as obtainable by or as obtained by the method as described in anyone of embodiments 101-174 as a component of a medical implant or as a medical implant.
205. Use as a component of a medical implant or as a medical implant of an osteoconductive fibrous article of embodiments 202 or 203.
206. A method of making a medical implant, wherein a bioactive fibrous article of anyone of embodiments 201-203 is used as a component of the medical implant.
207. A medical device or implant comprising a bioactive fibrous article of anyone of embodiments 201-203, preferably as the part of the device or implant that will interface with bone.
208. The medical device or implant of embodiment 207, being a permanent high-strength orthopedic implant for repairing bone fractures or torn ligaments or tendons, preferably selected from the group consisting of flexible tissue anchors, cortical fixation devices like ACL loops, high-strength orthopedic sutures, bone cerclage cables, synthetic tendon and ligament grafts, interspinous spacers or spinal disc prostheses, spinal fusion devices, and synthetic scaffolds to repair bone voids.

The experiments and samples below further elucidate embodiments of the invention but should not be construed as in any way limiting the scope of the claims.

EXPERIMENTS

Methods
Substrate Preparation

Different coating experiments were performed on braided constructions of polyester yarn (PET), but in view of analytical aspects also on flat film PET material. As braided material, a flat braid (construction 32*1200 dtex) made from multi-filament PET yarns was used, or a braided construction of 12*200 dtex with 6.9 st/cm, mimicking the tubular anchor body of a Juggerknot® all-suture anchor. The braid ends of this second type of braid were melt-fused before cleaning to prevent fraying.

Samples were cleaned before further testing by submersing in hexane (Merck) and sonication during 5 minutes (Branson 5510 ultrasonic bath). The material was then rinsed by shaking with fresh hexane, followed by submersing in 96% ethanol (Merck) and sonication during 5 min. The material was then rinsed with 96% ethanol, and then dried in air at room temperature for at least 2 h.

PET film strips (Hostaphan®, Mitsubishi) were cleaned analogously to the braids before use.

Samples of JuggerKnot® soft anchors 1.4 and 2.9 mm (Zimmer Biomet), comprising braided sleeve and suture constructions based on multi-filament PET yarns, were used as received.

Coating with Polymer Solution and Bioceramics Dispersion

A 10 mass % stock solution of Bionate® PCU 80A, a thermoplastic polyurethane comprising aliphatic polycarbonate soft blocks of hardness 83 Shore A (DSM Biomedical) in THF (chromasolve unstabilized; VWR) was prepared and diluted with THF to make coating solutions for use in coating experiments.

Hydroxyapatite (HA; indicated primary particle size 200 nm; Premier Biomaterials) dispersions were prepared by adding the required amount of bioceramics to THF or water. The dispersion was mixed on a vortex VV3 for 1 minute, followed by sonication during 10 minutes. When used, the dispersion was stirred with a magnetic stirrer at such a speed that a small vortex formed on the surface of the dispersion, until samples were to be inserted. Dispersions of hydroxyapatite and β-tricalciumphosphate (bTCP; indicated primary particle size 1 µm; Premier Biomaterials) were prepared in the same way.

Coating Method 1

Cleaned PET braids (of about 40 mm length), soft anchors, or flat PET samples (of about 50*10 mm) were coated with polyurethane by dipping the sample manually in the solution for 1-2 seconds. The dipped samples were dried in air during 30 min (unless otherwise indicated). After drying the coated samples were dipped in a dispersion of HA or HA/bTCP, for 1-2 seconds and dried in air for 2 hours.

Coating Method 2

This method differs from method 1 only in that cleaned PET braids were pre-wetted by submersing the braid in THF for 10 seconds, followed by a drying period of 10 s after removing the braid from the solvent; before coating with polyurethane solution and treating with a dispersion of bioceramic particles.

Coating Method 3

In other experiments samples were coated using a Harland RDX automated dip coater. Cleaned PET braids were weighted, mounted in the dip coater, and lowered into the solution to completely submerge the braid for 1-10 s as specified in the experiments, before raising the sample from the solution at draw rate 5 cm/s. Coated braids were dried in air and the mass increase was determined. After drying the coated braids were weighted, mounted in the dip coater, and lowered into a bioceramics dispersion to completely submerge the braid for 1-10 s as specified in the experiments, before raising the sample from the solution. The dispersions used were stirred during the dip coating process to prevent settling of the bioceramics, using such stirring speed that material was dispersed throughout the medium and a small vortex formed in the surface. The coated and treated braids were dried in air and the mass increase was determined.

Alizarin Staining

Staining with Alizarin red as done using a solution of Alizarin red in water, prepared by adding 40 mmol of Alizarin red (Sigma Aldrich) to 400 ml double-distilled water. The pH of the solution was adjusted to 4.2 with 1.0 N sodium hydroxide. Double-distilled water was added to obtain a total volume of 500 ml. The solution was filtered through a 0.2 µm filter before use. Samples were inserted in the solution for 10 minutes, rinsed with demi-water and dried in air for 1 h. Color measurement on stained samples was done by reflectance measurements on a Perkin Elmer Lambda 1050 with a 150 mm integrating sphere. Samples were placed on a white plate in front of the reflectance port of the sphere. Settings used were range 350-850 nm; step size 5 nm; slit 5 nm, integration time 0.4 s, background calibration Calibrated Spectralon Standard. From the reflectance spectra the color parameters were calculated according to ASTM E308 assuming a 10° observer and a D65 illuminant. The thus obtained a* values are used for evaluating red color development on the samples upon staining.

TOF-SIMS Analysis

TOF-SIMS analyses were performed on PHI nanoTOF II equipment, applying below conditions to determine the signal counts for Ca and Ca—O signals on PET film samples:
  1. Gun settings: 400 µm dia, high flow, unbunched
  2. Mass range: 0-1850 Da (pos & neg)
  3. Image areas: 100×100 µm and/or 400×400 µm
  4. Image resolution: 512×512 pixels
  5. Number of frames: ≥8 (depending on counts measured) for spectra.

IR Analysis

IR analyses were performed on a Perkin-Elmer Spectrum 100 FT-IR spectrometer with ATR-IR.

EXAMPLES AND COMPARATIVE EXPERIMENTS

Effect of Dispersion Solvent

Cleaned PET film strips were dip coated with polyurethane and bioceramics dispersion with above described method 1. In Table 1 data are presented.

In FIG. 1 two pictures on samples Ex 1 and CE 2 are represented, which both show red coloring; indicative of HA being present. If a dispersion of HA in water was used, the distribution of HA on the coated surface was markedly less homogenous than resulting from using a dispersion in THF (Ex 1). A sample only coated with polyurethane did not show such extent of staining.

TOF-SIMS analysis of the surfaces showed the presence of HA, as concluded from significantly higher signal counts for Ca for Ex 1 and CE 2 compared to CE 3 and unmodified PET; and similar values as found for HA powder. Table 1 comprises results for calcium signal count.

Effect of Polymer Coating

Cleaned PET braids were coated with polyurethane solutions of different concentrations applying method 1, followed by treatment with HA dispersions in THF or water. Alizarin red staining confirmed presence of HA on all samples made. It was then observed that after a tape test, wherein a Scotch office tape was pressed onto the modified braid surface and removed in a fast movement, the braid coloring was decreased for the water-based dispersion and the tape had red particles attached to it; whereas this was not or hardly observed for the THF-based dispersions. This indicates better adhesion of HA particles to the fibers when the coated braid is treated with a dispersion made with a solvent for the polyurethane coating. Samples treated with aqueous dispersion do comprise particles, but the particles appear to be merely physically entrapped between fibers and not adhered in or at their surface; as observed on SEM micrographs.

The samples were also analyzed by IR spectroscopy. In Table 1 the ratio of integrated areas of signals representing hydroxyapatite (1156–916 $cm^{-1}$) and PET (1764–1621 $cm^{-1}$; typical for the carbonyl group) are given; confirming presence of HA. The signal ratios for the coated samples made with different amounts of polymer are comparable, see Ex 2, 3 and 4. A relatively low amount of polyurethane or a thin coating layer is apparently already effective for modifying the surface.

Amount of Polymer and HA on Substrate

To determine the amount of polyurethane and HA deposited on the braids, the ends of cleaned braids ends were melt fused to avoid unravelling. Eight (8) samples were coated with method 3, using a 2.5 mass % solution of Bionate® PCU 80A in THF; and then treated with 9.1 mass % dispersion of HA in THF. Residence time in polyurethane solution was 10 s, pull-out rate 1 cm/s, drying time after coating was 30 minutes. Residence time in HA dispersion was 2 s, pull-out rate 1 cm/s, followed by drying in air for 2 h. The samples were weighted before and after the coating steps. Table 2 below shows the increase in mass % for the both steps as well as to total mass increase of the coated and treated article.

In FIG. 2, a SEM image of the surface of a coated fiber of Ex 5-1 sample is represented, showing HA particles exposed at the surface, while also being partially in the surface polymer layer. For such analysis a small piece was cut from the coated PET braid and placed on a double-side carbon tape. The surface was coated with an 8 nm iridium layer before placing it in the SEM apparatus.

TABLE 1

| | Type of PET sample | Polymer in coating solution (mass %) | Solvent for bioceramic dispersion | HA in bioceramic dispersion (mass %) | Observation after Alizarin red staining | TOF-SIMS signal count for calcium | IR signal ratio HA/PET |
|---|---|---|---|---|---|---|---|
| Ex 1 | Film | 2.5 | THF | 9.1 | Homogenous dark red coloring | 3364 | |
| CE 2 | Film | 2.5 | water | 9.1 | Inhomogeneous red coloring | 3725 | |
| CE 3 | Film | 2.5 | — | — | Slight coloring | 11 | |
| Ex 2 | Braid | 0.5 | THF | 9.1 | Red coloring | | 4.3 |
| Ex 3 | Braid | 1.0 | THF | 9.1 | Red coloring | | 3.5 |
| Ex 3-2 | Braid | 1.0 | THF | 9.1 | | | 3.4 |
| Ex 3-2 | Braid | 1.0 | THF | 9.1 | | | 3.5 |
| Ex 3-4 | Braid | 1.0 | THF | 9.1 | | | 3.5 |
| Ex 4 | Braid | 2.5 | THF | 9.1 | Red coloring | | 4.3 |
| CE 4 | Braid | — | THF | 9.1 | | | 0.1 |
| CE 5 | Braid | — | water | 9.1 | | | 0.1 |
| CE 6 | Braid | 0.5 | water | 9.1 | Red coloring | | |
| CE 7 | Braid | 1.0 | water | 9.1 | Red coloring | | 5.6 |
| CE 8 | Braid | 2.5 | water | 9.1 | Red coloring | | 5.0 |

TABLE 2

| Example | Mass increase after polymer coating (%) | Mass increase after bioceramics treatment (%) | Total mass increase (%) |
|---|---|---|---|
| 5-1 | 1.6 | 1.5 | 3.0 |
| 5-2 | 1.6 | 1.7 | 3.3 |
| 5-3 | 1.5 | 1.1 | 2.7 |
| 5-4 | 1.6 | 1.5 | 3.1 |
| 5-5 | 1.6 | 1.4 | 3.0 |
| 5-6 | 1.7 | 1.2 | 2.9 |
| 5-7 | 1.5 | 1.1 | 2.6 |
| 5-8 | 1.5 | 1.5 | 3.0 |
| Average | 1.6 | 1.4 | 2.9 |
| St dev | 0.1 | 0.4 | 0.2 |

Adhesion of HA Particles

Samples made in Ex 3 were placed in 25 ml ethanol and sonicated during 1, 5 and 10 min. Then IR spectra were recorded and the areas representing hydroxyapatite (1156-916 cm$^{-1}$) and PET (1764-1621 cm$^{-1}$) were integrated. In Table 1 the respective ratios are listed for Ex 3-2, 3-3 and 3-3. The ratios appear not to be affected by this treatment, suggesting good adhesion of the particles to the coated braids The samples of experiments Ex 4 and CE 4 were submitted to a Scotch® tape test to assess adhesion of HA to the coated braids. IR-spectra were recorded before and after the tape test and the ratios of areas representing hydroxyapatite and PET were determined as above. The results summarized in Table 3 confirm adhesion of HA particles to the fibrous article.

TABLE 3

| Polymer in coating solution (mass %) | Ratio of signal areas of HA to PET | |
|---|---|---|
| | before tape test | after tape test |
| — | 0.1 | 0.1 |
| 2.5 | 4.3 | 3.6 |

Cleaned braid samples were coated using method 1 with Bionate® PCU 80A as coating polymer and treated with HA dispersion in THF as described above. Samples were submitted to a tape test and stained with Alizarin red. Color measurements were performed resulting in the a* values indicative for red color intensity as shown in Table 4. A blank PET sample and a sample with only coating polymer were used as comparatives. The samples were prepared and measured in duplicate. The color measurements confirm binding of HA particles to the coating layer, showing good adhesion of HA (little effect of the tape test).

TABLE 4

| Experiment | Sample stained with Alizarin red | a* value sample 1 | a* value sample 2 |
|---|---|---|---|
| CE 9 | PET | 1.57 | 3.37 |
| CE 10 | PET polymer coated | 11.43 | 9.30 |
| Ex 6-1 | PET polymer/HA coated | 24.43 | 20.06 |
| Ex 6-2 | PET polymer/HA coated; after tape test | 23.32 | 21.41 |

Effect of Concentration Bioceramic Dispersion

The effect of the concentration of hydroxyapatite dispersions in THF on the amount of hydroxyapatite deposited on the coated PET braids was investigated by coating PET braids according to method 2; using a 2.5 mass % solution of Bionate® 80A in THF and 5, 10, 15 and 20 mass % HA dispersions in THF. A higher hydroxyapatite concentration also resulted in an increased amount of HA on the PET braid, which appears to level off above 15 mass %. IR analysis confirmed an increased coverage of the surface by hydroxyapatite. Table 5 shows the results of this series of experiments.

TABLE 5

| Experiment | [HA] (mass %) | Mass gain (%) | Average (%) | St dev. |
|---|---|---|---|---|
| Ex 7.1 | 5 | 3.7 | 3.4 | 0.2 |
| Ex 7.2 | 5 | 3.5 | | |
| Ex 7.3 | 5 | 3.4 | | |
| Ex 7.4 | 5 | 3.2 | | |
| Ex 7.5 | 10 | 5.9 | 6.1 | 0.9 |
| Ex 7.6 | 10 | 5.1 | | |
| Ex 7.7 | 10 | 6.3 | | |
| Ex 7.8 | 10 | 7.2 | | |
| Ex 7.9 | 15 | 16.2 | 15.2 | 0.8 |
| Ex 7.10 | 15 | 14.4 | | |
| Ex 7.11 | 15 | 14.6 | | |
| Ex 7.12 | 15 | 15.5 | | |
| Ex 7.13 | 20 | 15.2 | 16.3 | 1.4 |
| Ex 7.14 | 20 | 15.2 | | |

TABLE 5-continued

| Experiment | [HA] (mass %) | Mass gain (%) | Average (%) | St dev. |
|---|---|---|---|---|
| Ex 7.15 | 20 | 17.1 | | |
| Ex 7.16 | 20 | 17.9 | | |

Pull-Out Force

JuggerKnot® ASA samples (part #912529; Zimmer Biomet) were dip coated using method 1 with a 2.5 mass % solution of Bionate® PCU 80A in THF and treated with a 9.1 mass % dispersion of HA in THF. The ASA samples, coated and uncoated, were inserted into foam blocks as described in the manufacturer's instruction for uncoated anchors.

Pull-out tests were performed on 4 unmodified (CE11) and 4 surface-modified (Ex 8) ASA samples, using biphasic polyurethane foam blocks ("bone foam", Sawbones) to simulate physiologic bone (see for example Brand (DOI: 10.1016/j.arthro.2017.01.012) or Barber (DOI: 10.1016/j.arthro.2016.09.031)). The foam blocks have indicated bulk density of 20 pcf, and a 2 mm thick top layer with density of 40 pcf (pcf=lbs/cf=lb/ft$^3$=16.02 kg/m$^3$). This type of bone foam was selected to investigate if the coating applied to the ASA device could decrease mechanical pull-out strength when anchor pull-out is the prevailing failure mode (versus suture rupture).

Samples were carefully installed into bone foam blocks (l*w*h=31*31*42 mm), one sample per block; using the ASA manufacturer's instructions along with the manufacturer's installation kit (Zimmer Biomet—part #912057).

Pull-out tests were performed on a universal test machine (Instron 5565A) equipped with a load cell of 1 kN, using a pull speed of 400 mm/min (no pre-load). Foam blocks with embedded ASA samples were placed into a test fixture holder mounted on the lower column of the test machine, and the high-strength sutures were clamped in a pneumatic horn grip mounted on the upper column of the test machine. Tension was applied on the embedded ASA device via the high-strength sutures until failure, defined as >80% drop in tension. The maximum recorded force was recorded. All samples failed by the PET anchor being pulled-out of the bone foam tunnel versus rupture of the high-strength sutures. There was no meaningful difference in the average maximum pull-out force values between the unmodified control samples and the coated samples, showing that the polyurethane/HA coating did not adversely affect the mechanics of the native PET fibrous anchor component (see Table 6).

In another series, similar pull-out measurements were performed with foam blocks having an indicated bulk density of 20 pcf and a 3 mm thick top layer of 50 pcf. Anchors were coated manually with a 2.5 mass % solution of Bionate® PCU 80A in THF and treated with a 9.1 mass % dispersion of HA in THF. Anchor installation and pull-out measurements were as described above. The maximum force measured was at breakage of the suture rather than at pulling the anchor from the foam block; see Table 7.

TABLE 6

| Experiment | Max. pull-out force (N) |
|---|---|
| CE 11-1 | 138 |
| CE 11-2 | 255 |
| CE 11-3 | 292 |
| CE 11-4 | 290 |

TABLE 6-continued

| Experiment | Max. pull-out force (N) |
|---|---|
| Average (st dev) | 244 (72) |
| Ex 8-1 | 263 |
| Ex 8-2 | 270 |
| Ex 8-3 | 226 |
| Ex 8-4 | 229 |
| Average (st dev) | 247 (23) |

TABLE 7

| Experiment | Max. pull-out force (N) | remark |
|---|---|---|
| Ex 9.1 | 619 | Suture breakage |
| Ex 9.2 | 552 | Suture breakage |
| average | 586 | |

Mechanical Properties

In another series of experiments mechanical properties and effect of coating method were investigated, as presence of the TPU/bioceramics coating may affect for example stiffness of the braids, which might have an influence on the initial hold force of an anchor when deployed.

Braids coated according to coating methods 1 and 2, and their stiffness was compared to uncoated braids with 2 different methods. In the first method braids of approx. 20 cm were coated; and after the coating process and drying the melt-fused braid ends were removed. The remaining part was then subjected to a free bending test, wherein one of the braid ends was horizontally fixated and the vertical displacement by gravity versus the initial horizontal position of the other free braid end was measured for a braid length of 15 cm. In addition, some of the coated samples were mechanically loaded by manually bending, stretching, compressing and wrenching over the longitudal axis of the braids. In Table 8 results from these tests are summarized. The applied mechanical loading of coated braids was found to undue a stiffening effect of the applied coating; and was checked to cause no loss in mass (no indication for HA being removed).

TABLE 8

| Experiment | Coating method | Displacement (cm) |
|---|---|---|
| Ex 10.1 | uncoated | 7.5 |
| Ex 10.2 | uncoated | 7.5 |
| Ex 10.3 | 1 | 2 |
| Ex 10.4 | 1 | 1 |
| Ex 10.5 | 2 | 3 |
| Ex 10.6 | 2 | 4.5 |
| Ex 10.3 after mechanically loading | 1 | 5 |
| Ex 10.5 after mechanically loading | 2 | 8 |

In another mechanical test, uncoated PET braids and coated PET braids that were coated according to coating method 1 and according to method 2, were submitted to a tensile test. The test was performed on a Z010 MultiXtens tensile tester with a pneumatic grip of 10 kN using a preload of 1 N and a test speed of 10 mm/min. For comparison, PET braids coated with only Bionate 80A, according to coating methods 1 and 2, were tested. The tensile test was performed to a strain of approx. 25%. From the test results, the modulus was derived from 0.3 to 0.8% strain. The results depicted in Table 9 show an increase in stiffness upon coating, which appears to be mainly caused by the TPU. PET braids that are coated with method 2 including a pre-wetting step show lower stiffness than when method 1 was used. Solvent already present within the braid apparently reduces or prevents internal coating with polymer.

In addition to the tensile test, an oscillating tensile test was performed wherein the strain was oscillated from 0-10%. From the test results the modulus was derived after the first, second and third cycle using the stress at 0.3-1% strain. The results shown in Table 10 clearly show that after the first loading the stress at 10% strain and the modulus are similar compared to uncoated PET braids. This shows that a bioceramic coating can be applied to a fibrous article without adversely affecting flexibility.

TABLE 9

| Experiment | Coating | Coating method | E-Modulus (MPa) | Average (MPa) | St dev |
|---|---|---|---|---|---|
| Ex 11.1 | uncoated | | 54.4 | 56.7 | 6.1 |
| Ex 11.2 | uncoated | | 46.3 | | |
| Ex 11.3 | uncoated | | 68.6 | | |
| Ex 11.4 | uncoated | | 57.6 | | |
| Ex 11.5 | Bionate | 1 | 161.5 | 223.2 | 35.7 |
| Ex 11.6 | Bionate | 1 | 245.1 | | |
| Ex 11.7 | Bionate | 1 | 263.1 | | |
| Ex 11.8 | Bionate | 2 | 128.5 | 126.8 | 13.4 |
| Ex 11.9 | Bionate | 2 | 144.2 | | |
| Ex 11.10 | Bionate | 2 | 107.7 | | |
| Ex 11.11 | Bionate/HA | 1 | 156.4 | 174.8 | 15.2 |
| Ex 11.12 | Bionate/HA | 1 | 201.3 | | |
| Ex 11.13 | Bionate/HA | 1 | 166.8 | | |
| Ex 11.14 | Bionate/HA | 2 | 188.7 | 177.4 | 7.1 |
| Ex 11.15 | Bionate/HA | 2 | 168.8 | | |
| Ex 11.16 | Bionate/HA | 2 | 174.7 | | |

TABLE 10

| Experiment | Coating | Coating method | Cycle | E-Modulus (MPa) | Stress at 10% strain (MPa) |
|---|---|---|---|---|---|
| Ex 12.1 | uncoated | | 1 | 55.9 | 64.6 |
| Ex 12.2 | uncoated | | 2 | 45.5 | 77.2 |
| Ex 12.3 | uncoated | | 3 | 57.1 | 98.7 |
| Ex 12.4 | Bionate | 1 | 1 | 145.7 | 54.8 |
| Ex 12.5 | Bionate | 1 | 2 | 43.3 | 57.1 |
| Ex 12.6 | Bionate | 1 | 3 | 36.4 | 60.9 |
| Ex 12.7 | Bionate | 2 | 1 | 98.1 | 55.1 |
| Ex 12.8 | Bionate | 2 | 2 | 41.7 | 65.2 |
| Ex 12.9 | Bionate | 2 | 3 | 32.2 | 66.1 |
| Ex 12.10 | Bionate/HA | 1 | 1 | 181.7 | 63.6 |
| Ex 12.11 | Bionate/HA | 1 | 2 | 47.0 | 69.3 |
| Ex 12.12 | Bionate/HA | 1 | 3 | 35.1 | 68.9 |
| Ex 12.13 | Bionate/HA | 2 | 1 | 145.3 | 66.5 |
| Ex 12.14 | Bionate/HA | 2 | 2 | 42.9 | 69.5 |
| Ex 12.15 | Bionate/HA | 2 | 3 | 35.0 | 70.2 |

In Vitro Study
Methods

Flat braids were constructed from PET yarn (approximately 5 mm wide and 1 mm thick; construction: 32*1200 dtex) and coated with bioceramics. Two bioceramic coating formulations were applied to the PET braids using the two-step Coating method 1: first, braids were dip-coated in a solution of Bionate® PCU 80A in THF (2.5 mass %), dried, and subsequently dip-coated in a dispersion of either (1) pure HA particles or (2) a mixture of HA/bTCP particles (80/20 mass ratio) in THF (10 mass %). After drying, samples were cut into 0.8 cm pieces and placed in a 48-well plate. Uncoated PET braid samples were similarly processed and served as a control reference. Sintered HA discs (3D Biotek) served as a positive control reference for an osteoconductive substrate. Test materials were cleaned and sterilized in ethylene oxide gas prior to cell culture.

Normal human bone marrow-derived mesenchymal stem cells (hMSCs; Lonza, PT2501, 22 year-old male) were thawed and expanded in basal cell culture medium containing serum (i.e. basal medium; Lonza, PT-3238) in culture flasks, with medium refreshment every 2-3 days. After 4 sub-passages, cells were trypsinized at approximately 80% confluency and used for cell culture experiments.

Material samples were placed in untreated 48-well culture plates designed for suspension culture to decrease cell adhesion to the culture plate rather than the material samples. Material samples were incubated in 300 µl basal medium overnight prior to cell seeding. The material samples were fixed to the bottom of the 48-well plates using cell crowns (Sigma-Aldrich) to prevent floating. After incubation, cell culture medium was removed, and cells were seeded by applying a suspension of 20,000 cells in 50 µl basal medium directly to the surface of each sample. Cells were also similarly cultured on tissue culture plastic as an internal control for normal cell behavior.

Cell-seeded material samples (i.e. test samples) were cultured in humidified incubators maintained at 37° C. and 5 vol % $CO_2$. After 4 hours of incubation, 250 µl of osteogenic medium (Osteogenic bullet kit, PT-3002, Lonza) was added to the wells. Test samples were cultured for 28 days with complete medium refreshment of 300 µl every 2-3 days.

Cell morphology was analyzed by SEM. Test samples were removed from their culture wells, rinsed in phosphate buffer solution (PBS), then dehydrated in a graded ethanol series followed by critical point drying in $CO_2$. Prior to SEM analysis, the samples were mounted on a conductive stub using conductive silver paint, then sputter-coated with a nano-layer of iridium. Micrographs were captured using a FEI Teneo microscope. Replicate (n=2) test samples were analyzed at day 28.

SEM-EDX was used to analyze biomineralization of the extracellular matrix produced by cells cultured on the test materials. Analysis was performed using a Versa 3D HR FEG-SEM equipped with an Everhart Thornley Detector (ETD, topography information), a concentrical back scatter detector (CBS, materials contrast information) and an EDAX TEAM elemental analysis detector at accelerating voltages of 5-10 kV.

Cell viability and DNA content of the test samples were measured after 7, 14, and 28 days culture. Assay measurements were performed in duplicate per test sample, and 4 replicate test samples (n=4) per material group were assayed at each time point.

The PrestoBlue assay (Invitrogen) was used to measure cellular metabolic activity as an indicator of viability at a given time point and cell and proliferation across multiple time points. At each time point, test samples were removed from their culture plates and transferred to fresh 48-well plates, rinsed in PBS to eliminate non-adhered cells, and incubated with PrestoBlue reagent for 30 minutes at 37° C., according to the manufacturer's instructions. Incubated reagent (200 µl) was transferred to a white 96-well plate for fluorescence detection using a multimode plate reader (BMG labtech Clariostar) set to 545 and 590 nm excitation/emission wavelengths, respectively (readout: relative fluorescent units, RFU).

For DNA assays, cell lysate was prepared as follows: test samples were removed from culture plates, transferred to a fresh multi-well plate, rinsed in PBS to remove non-adherent cells, freeze-thawed, and individually immersed in cell lysis buffer per the manufacturer's instructions (CyQuant cell lysis buffer, component C7026, Invitrogen). Cell lysate was then sampled separately for DNA and ALP assays.

The CyQuant assay (Invitrogen) was used to measure DNA content in test sample lysate following the manufacturer's instructions. A standard curve was prepared using DNA standard provided in the assay kit, ranging from 0 to 0.35 µg/µl DNA diluted in lysis buffer. Cell lysate or DNA standard (100 µl) was combined with GR-dye solution (1×, 100 µl) in a white 96-well plate, gently mixed, and incubated in for 15 minutes in the dark at room temperature prior to fluorescence measurement using a multimode plate reader (BMG labtech Clariostar), set to 480 and 500 nm excitation/emission wavelengths, respectively (readout: relative fluorescent units, RFU).

Results

Human mesenchymal stem cells were cultured on PET braids coated with Bionate® PCU 80A and bioceramic particles—either pure HA or a mixture of HA and bTCP—for 28 days. Both HA- and HA/bTCP-coated PET braids substantially enhanced cell viability versus uncoated PET after 28 days culture (see Table 11). HA-coated PET increased mean cell viability by more than 200% compared to the uncoated PET control. Whereas mean cell viability steadily increased on HA- and HA/bTCP-coated PET between 7 and 28 days (about 50% and 190% higher, respectively), cell viability on uncoated PET decreased by more than half during the same period. Notably, both HA and HA/bTCP coatings resulted in similar, if not higher, viability versus HA discs, a known osteoconductive substrate.

Similarly, both bioceramic coatings considerably enhanced cell proliferation and cell number on the PET braids, during the culture period as indicated by DNA content (see Table 12). By day 28, mean DNA content was about 85% and 180% higher on HA and HA/bTCP-coated PET, respectively, versus uncoated PET. DNA content on both coated-PET sample groups steadily increased between 7 and 28 days culture, whereas DNA content decreased by more than half on uncoated PET during the same period. Importantly, HA- and HA/bTCP coated PET samples promoted similar if not higher cell numbers, according to DNA content, versus HA discs, the positive control for an osteoconductive material.

Cell morphology and extracellular matrix (ECM) production after cell culturing were visually analyzed using SEM. FIG. 3 show biomineralization as evidenced by electron-dense nodules in HA- and HA/bTCP-coated samples and HA discs. After 28 days culturing, both HA and HA/bTCP coatings visibly enhanced cell attachment, spreading, and ECM production versus uncoated PET. Cell-secreted filamentous ECM more densely covered coated-PET; bioceramics loaded fibers appear to enhance cell number and attachment. Cell alignment facilitated by actin expression appeared to be guided along the fiber architecture suggesting topographical effects (e.g. of roughness) contributing to the response. Uncoated PET supported only modest cell adhesion; and only sparse cells spanning between fibers can be seen.

Figure 4A:
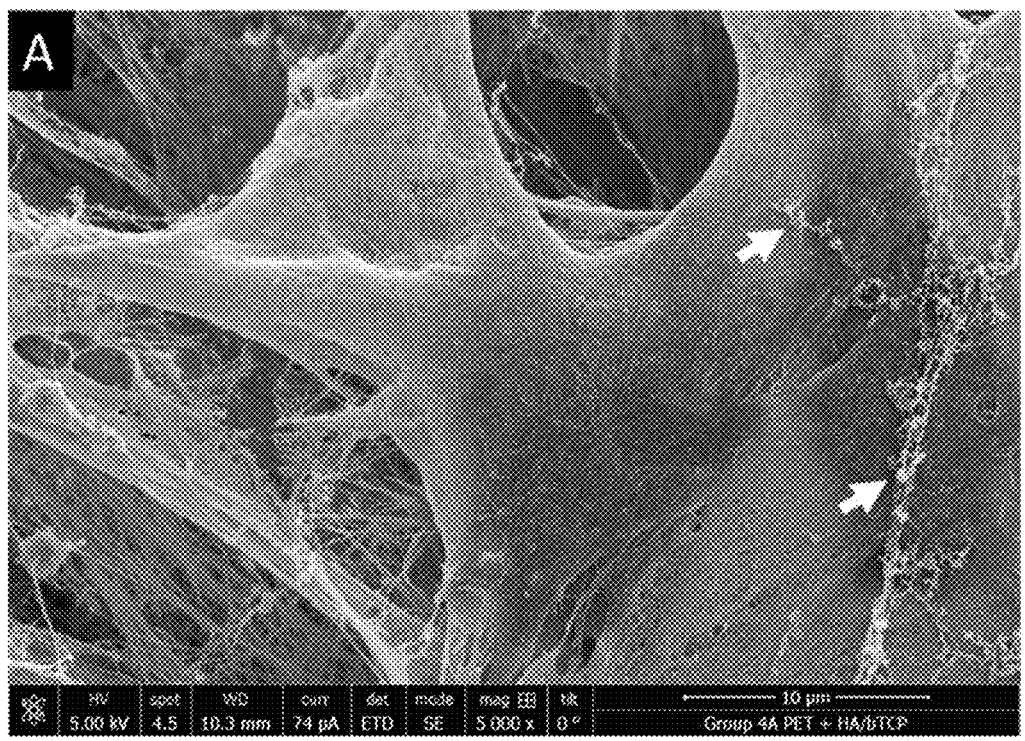
FIGS. 4A and 4B show high magnification SEM of hMSCs cultured on PET braids coated with a mixture of HA and bTCP.
Figure 4B:
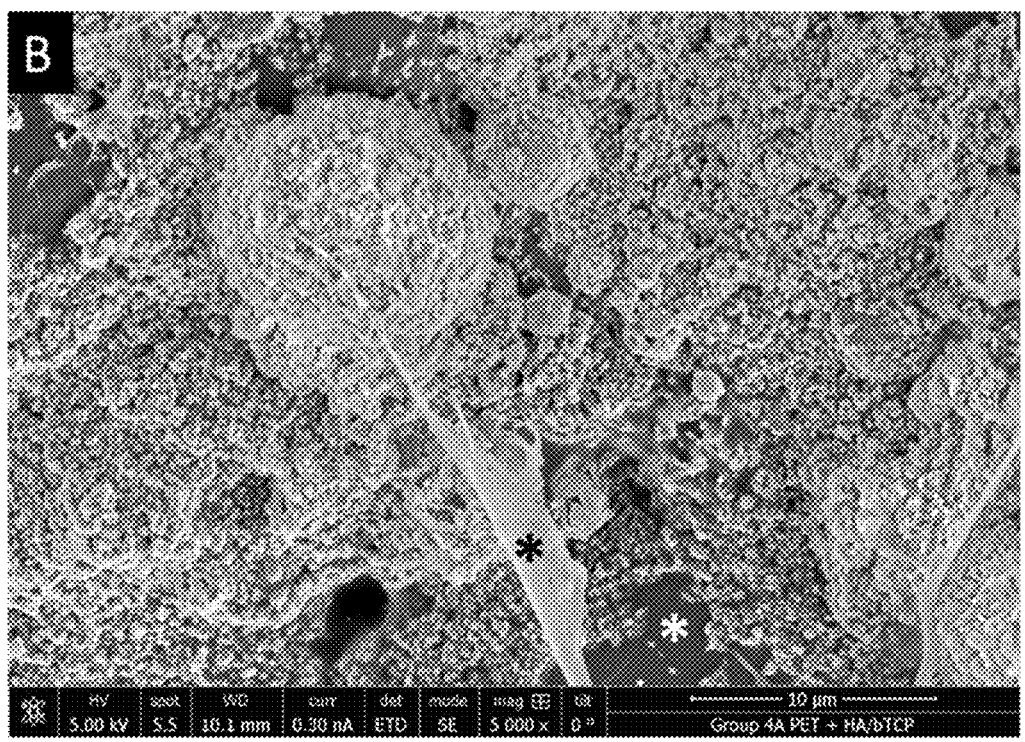

High magnification SEM of hMSCs cultured on PET braids shown in FIG. 4 show prolific cells and abundant extracellular matrix covering most of the coated braid surface. Small amounts of electron-dense mineral-like nodules resembling biomineralization (white arrows) were visible on the surface of some cells. In other locations, biomineralization in the form of electron-dense nodule propagation was evident directly on the coated surface (white asterisk), which supports cellular attachment (black asterisk).

Importantly, morphologic evidence of biomineralization—the genesis of bone tissue formation—was observed on HA- and HA/bTCP-coated PET samples, in the form of electron-dense micro-nodules in the ECM. Such nodules were sparse if not absent on uncoated PET control samples. The chemical composition of the ECM nodules was confirmed by EDX to be principally composed of calcium and phosphate, further substantiating its biomineralized nature.

In summary, bioceramic coatings, based on Bionate® 80A polyurethane and bioceramic particles, applied to PET fiber-based braided constructs were shown to enhance hMSC viability, proliferation, cell number, and ECM production versus uncoated PET. Notably, biomineralized nodule formation in the ECM indicated that stem cells were able to differentiate into functional osteoblast-like cells on the bioceramic coated PET samples but not on uncoated PET.

TABLE 11

| | | Cell viability (PrestoBlue assay; mean RFU) | | |
| --- | --- | --- | --- | --- |
| Experiment | Sample | Day 7 | Day 14 | Day 28 |
| CE 11 | PET (uncoated) | 114,201 +/− 27,364 | 18,322 +/− 985 | 53,897 +/− 11,752 |
| Ex 13 | PET coated with HA | 61,057 +/− 7,467 | 135,556 +/− 23,069 | 178,685 +/− 51,135 |
| Ex 14 | PET coated with HA/bTCP | 61,813 +/− 9,402 | 38,628 +/− 6,854 | 93,957 +/− 37,632 |
| CE 12 | HA Discs | 66,134 +/− 19,135 | 18,549 +/− 979 | 95,835 +/− 7,993 |

TABLE 12

| | | DNA content (CyQuant assay) of hMSCs cells cultured on test materials (ng/ml) | | |
| --- | --- | --- | --- | --- |
| Experiment | Sample | Day 7 | Day 14 | Day 28 |
| CE 13 | PET (uncoated) | 4.91 +/− 0.24 | 4.66 +/− 1.07 | 2.31 +/− 0.83 |
| Ex 15 | PET coated with HA | 2.07 +/− 0.93 | 3.43 +/− 0.63 | 4.27 +/− 0.96 |

TABLE 12-continued

| | | DNA content (CyQuant assay) of hMSCs cells cultured on test materials (ng/ml) | | |
|---|---|---|---|---|
| Experiment | Sample | Day 7 | Day 14 | Day 28 |
| Ex 16 | PET coated with HA/bTCP | 1.80 +/− 0.34 | 1.88 +/− 0.77 | 6.56 +/− 2.65 |
| CE 14 | HA Discs | 1.37 +/− 0.87 | 2.05 +/− 0.67 | 6.18 +/− 1.80 |

In Vivo Evaluation of Bioactivity

The bioactivity of the PU-based bioceramic coatings described herein was further tested in an animal model of bone repair. This feasibility study was designed to investigate the benefit of such a bioceramic coating on the osseointegration of relevant fiber-based orthopaedic implants, such as all-suture anchors, which are principally composed of PET and/or UHMWPE fibers. It has been reported that such fiber-based devices may loosen over time due to lack of bone bonding of the fiber-based anchor in the bony implantation site. To address this need, it was hypothesized that an all-suture anchor incorporating a bioactive surface coating would bond to bone better and increase the mechanical stability of the anchor in bone. Sheep were selected as the model species due to their general acceptance as an appropriate analogue to human bone structure and repair. Because all-suture anchors are most often clinically used for rotator cuff and glenoid labrum repair in the shoulder, this anatomical location was selected for implantation.

Methods

Sample Preparation

Samples were prepared from all-PET suture anchors, that is from commercially available 1.4 mm anchors (Zimmer Biomet, Juggerknot® soft anchors single loaded, article #912030) and 2.9 mm anchors (Zimmer Biomet, Juggerknot® soft anchors double loaded, article #912029) as received from the supplier in sterilized packaging. The anchor sheath part was slid to approximately 2 cm from the end of the sutures. In a first coating step the anchor sheaths were side-coated with polyurethane solution, instead of submersing the complete anchor (sheath and sutures), by placing about 1 ml of the Bionate® solution (2.5 mass % in THF) on a microscope object glass plate and contacting both sides of the anchor sheath shortly with the solution. After coating the anchors were dried in air for 30 minutes. The treatment with bioceramics was performed as in coating method 1. In this way anchors were coated with HA and a mixture of HA and Bioglass® (80/20, m/m; 'HA/BG' treatment) in THF. Dispersion of HA/Bioglass® in THF was prepared from 36 g of THF, 3.6 g of hydroxyapatite and 0.4 g of Bioglass®. Bioglass® refers to Bioglass® 45S5 powder, obtained from MO-SCI Health Care with lot #265-10-1-15289, indicated particle size d50 0.4 µm. After coating and drying the anchor sheaths were slid back to the middle of the sutures and packed in its original packing. The packaging was sealed and sterilized with ethylene oxide.

XPS Measurements

XPS-measurements on uncoated and coated Juggerknot® samples have been carried out in a Quantera SXM™ from ULVAC-PHI (Q1), using monochromatic AlKα-radiation and a take-off angle Θ of 45°. At these conditions the information depth is only approximately 7 nm. A spot size of 100 µm (25 Watt), scanned across an area of 300*300 µm was applied for the analyses. By means of wide-scan measurements the elements present at the surface have been identified; accurate narrow-scans have been measured for quantification. Standard sensitivity factors were used to convert peak areas to atomic concentrations. In view of this, it is possible that the concentrations deviate from reality in the absolute sense (generally not more than 20% relative). Coating methods described herein were thus applied to commercially available PET-fiber based all-suture anchors and verified that the coatings resulted in bioceramics exposed at the extreme surface of the coated anchor implants. The results collected in Table 13 indicate presence of Ca and P only at the surface of anchors that were coated with HA and Bioglass® (values given are averages of 4 measurements).

TABLE 13

| Experiment | Sample | Ca (atom %) | P (atom %) |
|---|---|---|---|
| Ex 17-1 | 2.9 mm anchor; | 0.9 ± 0.0 | 1.0 ± 0.1 |
| Ex 17-2 | Bionate/HA coated | 1.1 ± 0.5 | 0.8 ± 0.2 |
| Ex 18-1 | 1.4 mm anchor; | 1.4 ± 0.4 | 1.0 ± 0.3 |
| Ex 18-2 | Bionate/HA coated | 0.6 ± 0.2 | 0.4 ± 0.1 |
| Ex 19-1 | 1.4 mm anchor; | 0.9 ± 0.1 | 0.5 ± 0.1 |
| Ex 19-2 | Bionate/HA-Bioglass ® coated | 0.8 ± 0.3 | 0.5 ± 0.1 |
| CE 15-1 | 1.4 mm anchor; | <0.1 | not detected |
| CE 15-2 | Bionate coated | <0.1 | not detected |
| CE 16-1 | 1.4 mm anchor; | <0.1 | not detected |
| CE 16-2 | uncoated | 0.2 | not detected |

Implantation

Skeletally mature female sheep (Ovis aries; 64-88 kg) were randomly selected from a closed herd and ear tags for identification were assigned. Animals were administered analgesic (fentanyl and phenybutazone) pre-operatively to relieve pain. Antibiotics (penicillin) was also administered to prevent infection. Animals were fully anesthetized in dorsal recumbency immediately prior to surgery. The right forelimb of an animal was clipped of wool, aseptically prepped, and draped for surgery. A 12-inch incision was made over the point of the shoulder joint. Soft tissue was carefully incised exposing the lateral glenoid rim. Unilateral cylindrical bone defects were created in the lateral glenoid rim according to the all-suture anchor device manufacturer's instructions, using the tooling provided with the device. Four 2.9 mm Juggerknot all-suture anchors—either coated with HA/BG or uncoated (control)—were implanted in the glenoid defects per animal following the manufacturer's instructions. After each anchor was implanted and the tooling was removed, a 6.5 mm section of surgical tubing was placed over each of the high-strength sutures connected to the anchor and the sutures were knotted and cut just above the tubing to ensure the sutures could be retrieved for biomechanical testing after explantation. After implantations, incised connective tissue was reapproximated using 2-0 absorbable sutures. Stainless steel staples were then used to close the cutaneous incision.

After surgery, animals were monitored for recovery from anesthesia and allowed to resume full-weight bearing activity. Animals were housed indoors for two weeks before they were transferred to a closed pasture for the remainder of the study. During this period, animals were fed grass/alfalfa mix hay and provided tap water ad libitum.

At the 12-week post-implantation time point, animals were humanely euthanized by intravenous overdose of pentobarbitone sodium (~88 mg/kg). Implanted glenoid bones were surgically disarticulated from the joint, soft tissue was removed, and wrapped in saline-soaked gauze for immediate biomechanical testing or fixed in 10% neutral buffered formaldehyde (NBF) for histological processing.

Biomechanical Testing

The distal end of glenoid bones containing implants were potted in PVC sleeves and immobilized in epoxy resin. Following resin curing, potted bone samples were mounted in a servo-hydraulic testing machine (MiniBionix 858, MTS Systems) using a custom-designed fixture. High-strength sutures connected to the implanted anchor were fixed in an upper grip fixture attached to the actuator of the test machine with 30 mm gauge length between the grip and the surface of the bone.

Biomechanical testing included three phases: (i) pre-tensioning, (ii) cyclic loading, and (iii) ramp to failure. Ramp to failure is a destructive test and was performed as the last test in the evaluation sequence. For pre-tensioning, tensile load of 10 N was applied to the samples to remove any slack in the sutures. Following the preload, a cyclic load oscillating between 10 and 100 N was applied at 0.5 Hz for 100 cycles or until failure was observed. After completion of 100 cycles, tensile load was applied at a constant displacement rate of 12.5 mm/s for destructive ramp to failure. All loads were applied quasi-statically and aligned collinear to the implant via the sutures attached to the actuator of the testing system. Load (N) and cross-head displacement (mm) data were acquired at 100 Hz. For the cyclic load, displacements were calculated at cycles 1, 2, 10, 50, and 99, defined as the difference between maximum and minimum displacements for the given cycle. Ultimate load at failure, displacement at failure, stiffness, and mode of failure (M.O.F.) (i.e., anchor pull out, eyelet/suture cut out, or suture breakage) were calculated.

Histological Evaluation

Samples were removed from NBF and trimmed for subsequent histological processing. Once trimmed, samples were dehydrated through graded alcohols, cleared with xylene, processed for infiltration and polymerization of methyl methacrylate (MMA). Three sections per sample were made parallel to the long axis of the bone in order to capture cross-sections of the implanted all-suture anchors and surrounding bone (i.e., region of interest, ROI) spanning from most superficial to the deepest level of the anchor in the bone. The resulting sections were ground and polished using a grinding and polishing system (Exakt Technologies). Sections were ground to an approximate thickness of 100 μm and polished for surface staining. Sections were then stained with hematoxylin and eosin (H&E) and Stevenel's Blue (SB).

Histomorphometry analysis was performed on stained sections using Image-Pro® Plus 7 software under the supervision of a board-certified veterinarian pathologist. Analysis was conducted to measure the length of segments of bone in contact with the implanted anchor devices. The regions of interest (ROI) for analysis were marked on the digital images and the regions outside the ROI were masked. The area of the ROI was measured via a reverse mask. Using trace features, measurements were collected of the bone in contact with the device.

From these direct measurements on each histological section, the following morphometric parameters were calculated:
(i) Length of Bone in Contact with Implant Surface (mm)=Sum of all Bone in Contact length measurements; and
(ii) Percentage of Implant Surface with Bone in Contact (%)=(Total Bone in Contact Length)/(Total Implant Surface Length)*100.

General pathological evaluation for tissue response and biocompatibility of the implants was also conducted using a semi-quantitative approach (e.g., histological scoring).

Results

All animals were healthy and survived the end time point of 12 weeks with no complications.

Biomechanical testing showed that all-suture anchors incorporating the HA and Bioglass® coating (HA/BG) on the PET anchor displaced on average 44% less under cyclic loading through 99 cycles than without the coating (see Table 14, mean values +/−standard deviation of n=4 independent samples). These results indicate that the coated anchors were more firmly integrated in the glenoid bone than the uncoated anchors. After 100 cycles, ramp to failure tensile loading showed that mean ultimate strength was 30% higher for coated anchors versus uncoated anchors. Conversely, ultimate displacement at failure was 34% lower for coated anchors versus uncoated anchors. In conjunction, coated anchors were, on average, 42% stiffer than uncoated anchors (see Table 15, mean values +/−standard deviation of n=4 independent samples). In summary, the tensile strength and displacement under tensile loading was superior for anchors coated with bioceramics vs uncoated anchors, indicating that the coating enhanced the anchors' ability to integrate with the bone in a functionally beneficial way.

The advantage in mechanical performance of the coated all-suture anchors versus the uncoated, commercially available control could be considered a clinically relevant result, in particular displacement under cyclic loading. This difference, equating to roughly 4 mm less displacement, would conceivably enhance soft-tissue repair of the all-suture anchor in clinically applied procedures such as rotator cuff or labrum repair where sutured soft-tissue would apply tensile loading to the all-suture anchor in bone during physical activity.

Figure 5A:
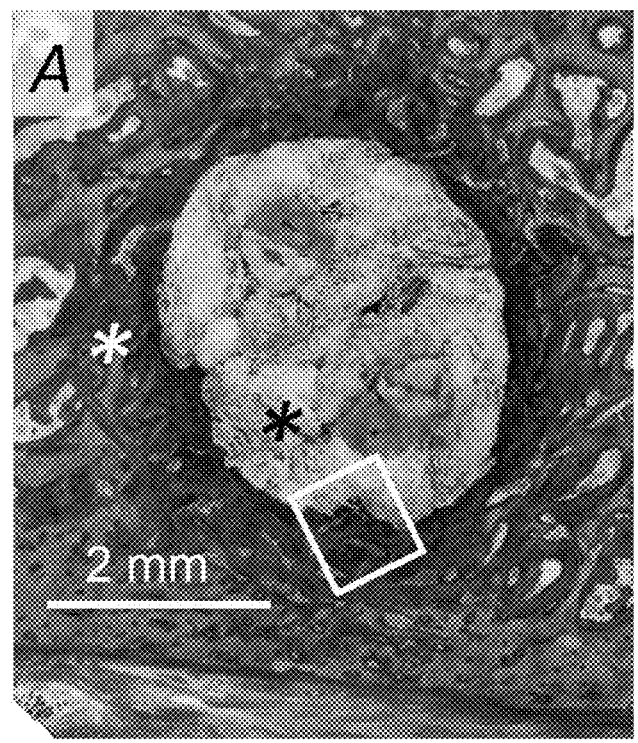
FIGS. 5A and 5B show representative histological micrographs of an ASA after having been implanted in sheep glenoid for 12 weeks. (A) Low magnification image depicting coated ASA (HA/BG); with almost the entire perimeter of the coated ASA (black asterisk) in direct contact with bone (white asterisk). (B) shows at higher magnification bone growth (black arrows) into the PET fiber structure of the anchor.
Figure 5B:
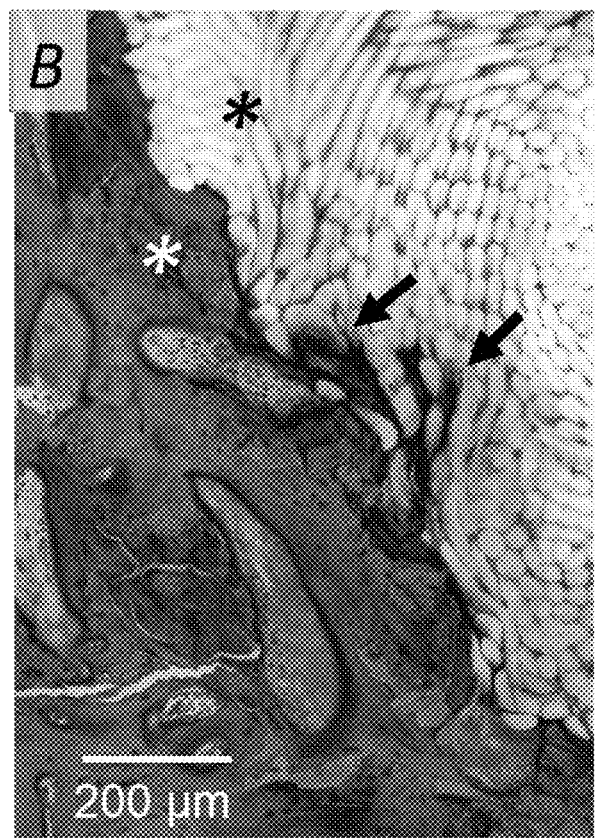

General histological evaluation demonstrated that both implant groups—coated and uncoated—were well tolerated in the glenoid and no adverse tissue reaction was observed. Histological sections were further analyzed by histomorphometry to evaluate if the coating could increase the bone-bonding ability of the all-suture anchor device. The length of bone in contact with the anchor was computed as a percentage of the anchor's perimeter and averaged across at least three histological sections per implant. In total, 4 implants per group (coated or uncoated) were analyzed. Bone in direct contact with the anchor was only observed for coated all-suture anchor samples (2 of 4 implants). Of the coated samples, on which direct bone contact was observed, the average length of bone in contact with the implant was ~about 27% of the implant perimeter (see Table 16). Representative micrographs are shown in FIG. 5, depicting bone in direct contact with the coated fibrous anchor and in some areas penetrating the fibrous construction. These results confirm the coating-enhanced bone deposition directly on the surface of the PET anchor. Moreover, these findings provide an explanation for the advantages observed in biomechanical testing—as more of the implant surface directly bonded to bone, the mechanical anchorage of the implant increased.

TABLE 14

| Cycle | Maximum displacement during cyclic tensile loading (mm) | |
|---|---|---|
| | Coated ASA (HA/BG) | Uncoated ASA (control) |
| 1 | 3.4 ± 1.7 | 5.3 ± 2.5 |
| 2 | 3.9 ± 2.0 | 6.5 ± 3.2 |
| 10 | 4.6 ± 2.4 | 8.2 ± 3.9 |
| 50 | 5.0 ± 2.6 | 9.0 ± 4.4 |
| 99 | 5.2 ± 2.7 | 9.3 ± 4.6 |

TABLE 15

| Result of cyclic tensile loading | Coated ASA (HA/BG) | Uncoated ASA (control) |
|---|---|---|
| Ultimate strength (N) | 539.7 ± 164.6 | 415.6 ± 167.2 |
| Ultimate displacement (mm) | 10.9 ± 5.2 | 16.6 ± 8.2 |
| Stiffness (N/mm) | 95.2 ± 28.4 | 67.2 ± 26.6 |

TABLE 16

| Histological analysis result | Coated ASA (HA/BG) | Uncoated ASA (control) |
|---|---|---|
| Frequency of bone-implant contact (n) | 2 of 4 | 0 of 4 |
| Bone-implant contact length (%) | 26.5 ± 32.0 | 0.0 ± 0.0 |

In summary, the HA/BG coating enhanced the biological activity and function of a commercially available all-suture anchor device in a simplified, non-loaded bone defect model in sheep. These results in the context of the study support the hypothesis that an osteoconductive coating could (1) enhance direct bone deposition (i.e. bonding) on an inert fiber substrate such as PET, and (2) osseointegration result in functional advantages such as decreased post-operative loosening and improved joint stability stemming from increased osseointegration of a fiber-based implant like an all-suture anchor.

Unless stated otherwise, any expression of mass % is based on the mass of the entire composition. It is noted that weight is still frequently used in the art instead of mass; mass and weight may herein be used interchangeably unless clearly contradicted by context.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as" or "like") provided herein, is intended merely to better illustrate the invention and does not pose a limitation on the scope of the invention unless otherwise claimed. No language in the specification should be construed as indicating any non-claimed element as essential to the practice of the invention.

Multiple embodiments of this invention or of certain aspects thereof are described herein, including preferred aspects and best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A method of making a bioceramic coating on a fibrous article for use in a medical implant comprising the steps of:
    a) providing an article comprising fibers made from a biocompatible, non-biodegradable polymer;
    b) coating at least a portion of the fibers of the article with a dispersion or solution of a non-biodegradable coating polymer in a first solvent for the non-biodegradable coating polymer to result in coated fibers having a layer of non-biodegradable coating polymer;
    c) treating the coated fibers by contacting the surface of the coated fibers by dip coating with a dispersion of bioactive ceramic particles of particle size 0.01-10 μm in a treating solvent comprising a second solvent for the non-biodegradable coating polymer in at least one step; and
    d) removing the treating solvent to allow at least a portion of the bioactive ceramic particles to extend above the layer of the non-biodegradable coating polymer and increase the mass of the coated fibers of the article by 0.1-15 mass %, and wherein at least a portion of the layer of non-biodegradable coating polymer is exposed at the surface of the article.

2. The method according to claim 1, wherein the fibrous article comprises fibers made from polyethylene terephthalate (PET).

3. The method according to claim 1, wherein a solution of coating polymer is used for coating the fibers and the solution comprises 0.1-10 mass % of coating polymer.

4. The method according to claim 1, wherein the non-biodegradable coating polymer is a thermoplastic elastomer and comprises a polyurethane block copolymer.

5. The method according to claim 4, wherein the polyurethane block copolymer comprises an aliphatic polycarbonate as soft block.

6. The method according to claim 1, wherein the bioactive ceramic particles comprise at least one of calcium phosphate and bioactive glass particles.

7. The method according to claim 6, wherein the bioactive ceramic particles have a particle size of 0.1-6 μm.

8. The method according to claim 1, wherein the bioactive ceramic particles comprise a mixture of calcium phosphate and bioactive glass particles.

9. The method according to claim 1, wherein the dispersion is substantially free of dispersion aids and surfactants.

10. The method according to claim 9, wherein the treating solvent further comprises a non-solvent for the non-biodegradable coating polymer, wherein the non-solvent for the coating polymer has a lower boiling point than the second solvent for the non-biodegradable coating polymer.

11. The method according to claim 1, wherein the medical implant comprises an orthopedic implant.

12. The method according to claim 11, wherein the orthopedic implant is a flexible tissue anchor, a cortical fixation device, an orthopedic suture, a bone cerclage cable, a synthetic tendon or ligament graft, an interspinous spacer or spinal disc prosthesis, a spinal fusion device, or a synthetic scaffold.

13. The method according to claim 11, wherein the medical implant is configured to interface with bone.

14. The method according to claim 1, further comprising the step of pretreating the article with a pre-wetting liquid comprising a solvent or a non-solvent for the coating polymer, wherein the pre-wetting liquid is a non-solvent for the biocompatible, non-biodegradable polymer.

15. The method according to claim 1, wherein the particle dispersion is devoid of coating polymer.

16. The method according to claim 1, wherein the first solvent is the same as the second solvent.

17. The method according to claim 1, wherein the dip coating comprises at least two dip coating steps.

18. The method according to claim 1, wherein the step of coating at least a portion of the fibers of the article with a dispersion or solution of a non-biodegradable coating polymer in a first solvent for the non-biodegradable coating polymer comprises a coating withdrawal rate from the dispersion or solution of 5 cm/sec or less.

19. The method according to claim 1, wherein the fibrous article is a flexible tissue anchor, or a sleeve component thereof.

20. The method according to claim 1, wherein the step of removing the treating solvent comprises evaporating the treating solvent.

21. The method according to claim 1, wherein a plurality of the bioactive ceramic particles are embedded in the layer of non-biodegradable coating polymer after the step of removing the treating solvent.

22. The method according to claim 1, wherein a plurality of bioactive ceramic particles are adhered to the layer of non-biodegradable coating polymer after the step of removing the treating solvent.

* * * * *